United States Patent
Steinkühler et al.

(10) Patent No.: US 6,197,536 B1
(45) Date of Patent: Mar. 6, 2001

(54) METHODOLOGY TO PRODUCE, AND PURIFY AND ASSAY POLYPEPTIDES WITH THE PROTEOLYTIC ACTIVITY OF THE HCV NS3 PROTEASE

(75) Inventors: Christian Steinkühler; Antonello Pessi; Elisabetta Bianchi; Marina Taliani; Licia Tomei; Andrea Urbani, all of Rome; Raffaele De Francesco, Marino; Frank Narjes, Ariccia, all of (IT)

(73) Assignee: Istituto di Ricerche di Biologia Moleculare S.p.A., Pomezia (IT)

( * ) Notice: Subject to any disclaimer, the term of this patent is extended or adjusted under 35 U.S.C. 154(b) by 0 days.

(21) Appl. No.: 09/011,961

(22) Filed: Feb. 23, 1998

(30) Foreign Application Priority Data

Aug. 22, 1995 (IT) ............................................. RM95A0573

(51) Int. Cl.$^7$ .............................. C12Q 1/37; A61K 38/00
(52) U.S. Cl. ............................................. 435/23; 530/323
(58) Field of Search ......................... 435/23, 219; 436/34; 530/323, 326, 328

(56) References Cited

U.S. PATENT DOCUMENTS 5,767,233 * 6/1998 Zhang et al. ......................... 530/326

FOREIGN PATENT DOCUMENTS

| 0 729 973 | 9/1996 | (EP) . |
| WO 91/15575 | 10/1991 | (WO) . |

OTHER PUBLICATIONS

Walsh, C. in "Enzyme Reaction Mechanism" W. H. Freeman and Company, San Francisco, pp. 56–84, 1979.*
Matayoshi et al. "Novel Fluorogenic substrate for assaying retroviral proteases by resonance energy transfer" Science 247, 954–958, Feb. 1990.*

Database WPI, Section Ch, Week 9642, Derwent Publications Ltd., London, GB; Class B04, AN 96–419825, XP002028745 & JP 08 205 893 A (Sumitomo Metal Ind Ltd), Aug. 13, 1996.
Journal of Clinical Investigation, vol. 96, 1995, pp. 224–230, XP000196704. Enomoto N. et al., "Comparison of full length sequences of interferon–sensitive and resistant hepatitis C virus 1b.".
Virus Research, vol. 23, 1992, pp. 39–53, XP000196705. Tanaka Y. et al., "Molecular cloning of Hepatitis C virus genome from a single Japanese carrier: sequence variation within the same individual and among infected individuals.".
Journal of Virology, vol. 68, No. 6, 1996, pp. 3753–3760, XP000577108. Failla, Chrisina et al., "Both NS3 and NS4A are required for proteolytic processing of hepatitis C virus nonstructural proteins.".
Journal of Virology, vol. 67., No. 7, 1993, pp. 4017–4026, XP000601449. Tomei, Licia et al., "NS3 is a serine protease required for processing of hepatitis C virus polyprotein.".

* cited by examiner

Primary Examiner—Nashaat T. Nashed
(74) Attorney, Agent, or Firm—Browdy and Neimark

(57) ABSTRACT

The process according to the present invention allows expression and isolation of polypeptides with the proteolytic activity of HCV NS3 protease in a pure, catalytically active form, and in amounts that are sufficient for discovery of NS3 protease inhibitors and for determination of the three-dimensional structure of the NS3 protease. A further subject of the present invention is a procedure that defines the chemical and physical conditions necessary for completion of the proteolytic activity of the above polypeptides. The invention further comprises new compositions of matter (expression vectors) containing nucleotide sequences capable of expressing the above mentioned polypeptides in culture cells. Finally, new compounds of matter are defined, suitable to measure the above proteolytic activity, and useful to develop NS3 protease inhibitors and therefore therapeutic agents for use against HCV. The figure shows the kinetic parameters of HCV NS3 protease using the S3 depsipeptide substrate (SEQ ID NO:45).

8 Claims, 13 Drawing Sheets

P<sub>ETL</sub> = PROMOTER OF THE GENE ENCODING THE PCNA PROTEIN
P<sub>PH</sub> = POLYHEDRIN PROMOTER
AMP = GENE ENCODING β-lactamase (AMPICILLIN RESISTANCE)
LacZ (β-gal) = GENE ENCODING β-galactosidase
Col E1 = pBR322 ORIGIN OF REPLICATION

FIG. 2a
pT7-7NS3 (1039-1226)
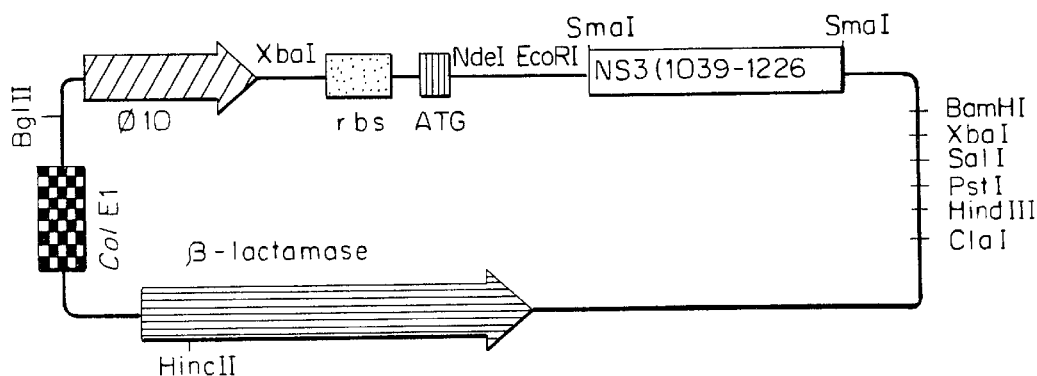
pT7-7NS3 (1039-1206)
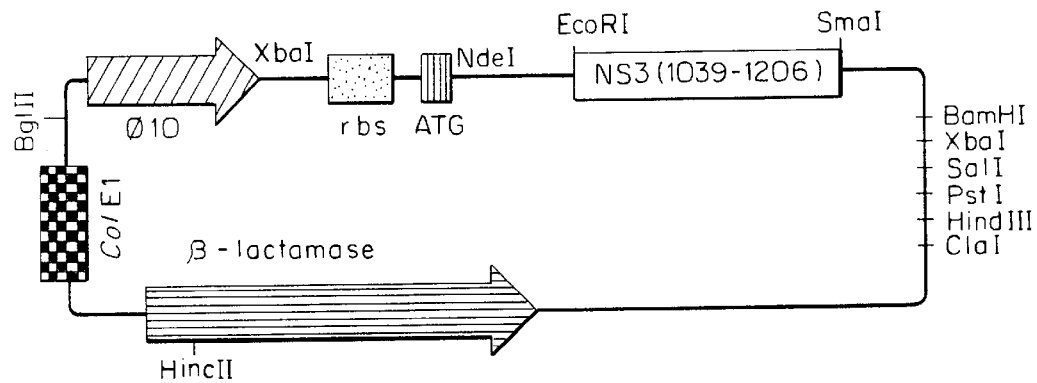
- Ø10 = Ø10 PROMOTER OF BACTERIOPHAGE T7
- rbs = SHINE-DALGARNO RIBOSOME BINDING SEQUENCE
- ATG = TRANSLATION INITIATION SITE OF THE PROTEIN ENCODED BY GENE 10 OF BACTERIOPHAGE T7
- β-lactamase = GENE ENCODING β-lactamase (AMPICILLIN RESISTANCE)
- Col E1 = pBR322 ORIGIN OF REPLICATION

FIG. 2b
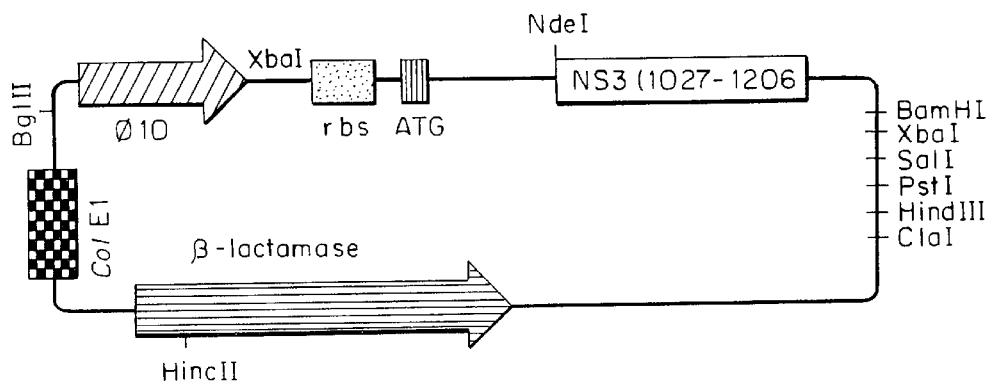
pT7-7NS3 (1027-1206)
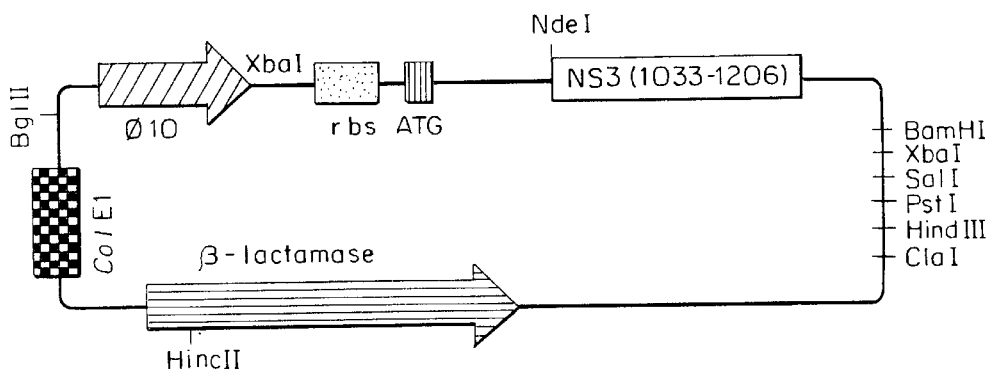
pT7-7NS3 (1033-1206)
Ø10 = Ø10 PROMOTER OF BACTERIOPHAGE T7
rbs = SHINE-DALGARNO RIBOSOME BINDING SEQUENCE
ATG = TRANSLATION INITIATION SITE OF THE PROTEIN ENCODED BY GENE 10 OF BACTERIOPHAGE T7
β-lactamase = GENE ENCODING β-lactamase (AMPICILLIN RESISTANCE)
Col E1 = pBR322 ORIGIN OF REPLICATION

GLYCEROL DEPENDENCE OF NS3 ACTIVITY

CHAPS DEPENDENCE OF NS3 ACTIVITY

FIG. 12
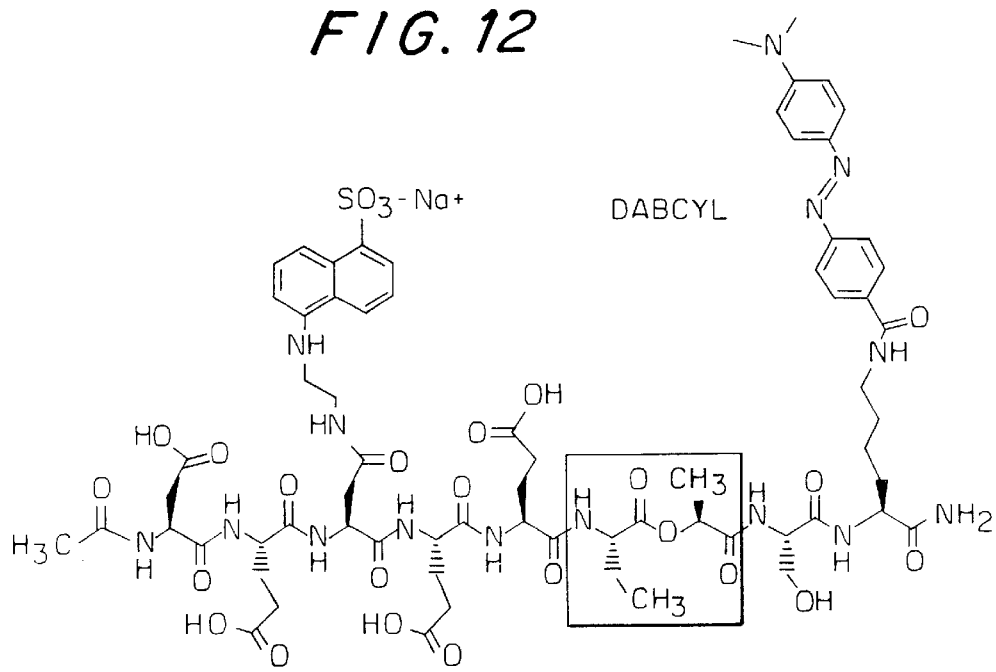
Ac-DED(EDANS)EEAbuΨ[COO]ASK(DABCYL)S3
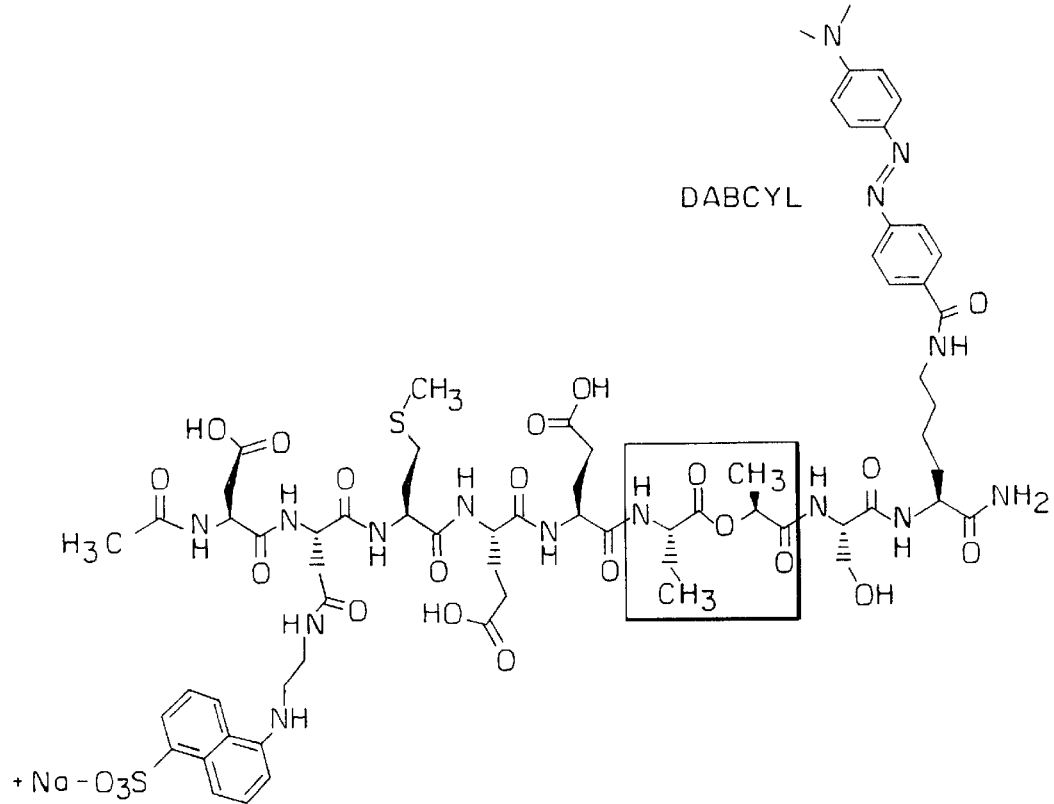
Ac-DD(EDANS)MEEAbuΨ[COO]ASK(DABCYL)S4

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 191 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:1:

```
Met Gly Leu Leu Gly Cys Ile Ile Thr Ser Leu Thr Gly Arg Asp Lys
1               5                   10                  15

Asn Gln Val Glu Gly Glu Val Gln Val Val Ser Thr Ala Thr Gln Ser
            20                  25                  30

Phe Leu Ala Thr Cys Val Asn Gly Val Cys Trp Thr Val Tyr His Gly
            35                  40                  45

Ala Gly Ser Lys Thr Leu Ala Gly Pro Lys Gly Pro Ile Thr Gln Met
50                  55                  60

Tyr Thr Asn Val Asp Gln Asp Leu Val Gly Trp Gln Ala Pro Pro Gly
65                  70                  75                  80

Ala Arg Ser Leu Thr Pro Cys Thr Cys Gly Ser Ser Asp Leu Tyr Leu
            85                  90                  95

Val Thr Arg His Ala Asp Val Ile Pro Val Arg Arg Arg Gly Asp Ser
            100                 105                 110

Arg Gly Ser Leu Leu Ser Pro Arg Pro Val Ser Tyr Leu Lys Gly Ser
            115                 120                 125

Ser Gly Gly Pro Leu Leu Cys Pro Ser Gly His Ala Val Gly Ile Phe
130                 135                 140

Arg Ala Ala Val Cys Thr Arg Gly Val Ala Lys Ala Val Asp Phe Val
145                 150                 155                 160

Pro Val Glu Ser Met Glu Thr Thr Met Arg Ser Pro Val Phe Thr Asp
            165                 170                 175

Asn Ser Ser Pro Pro Ala Val Pro Gln Ser Phe Gln Val Ala Leu
            180                 185                 190
```

(2) INFORMATION FOR SEQ ID NO:2:

(i) SEQUENCE CHARACTERISTICS:
(A) LENGTH: 195 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

```
Met Ala Arg Ile Arg Ala Leu Leu Gly Cys Ile Ile Thr Ser Leu Thr
1               5                   10                  15

Gly Arg Asp Lys Asn Gln Val Glu Gly Glu Val Gln Val Val Ser Thr
            20                  25                  30

Ala Thr Gln Ser Phe Leu Ala Thr Cys Val Asn Gly Val Cys Trp Thr
            35                  40                  45

Val Tyr His Gly Ala Gly Ser Lys Thr Leu Ala Gly Pro Lys Gly Pro
50                  55                  60

Ile Thr Gln Met Tyr Thr Asn Val Asp Gln Asp Leu Val Gly Trp Gln
65                  70                  75                  80

Ala Pro Pro Gly Ala Arg Ser Leu Thr Pro Cys Thr Cys Gly Ser Ser
            85                  90                  95

Asp Leu Tyr Leu Val Thr Arg His Ala Asp Val Ile Pro Val Arg Arg
            100                 105                 110

Arg Gly Asp Ser Arg Gly Ser Leu Leu Ser Pro Arg Pro Val Ser Tyr
```

```
                115                 120                 125
Leu Lys Gly Ser Ser Gly Gly Pro Leu Leu Cys Pro Ser Gly His Ala
    130                 135                 140

Val Gly Ile Phe Arg Ala Ala Val Cys Thr Arg Gly Val Ala Lys Ala
145                 150                 155                 160

Val Asp Phe Val Pro Val Glu Ser Met Glu Thr Thr Met Arg Ser Pro
                165                 170                 175

Val Phe Thr Asp Asn Ser Ser Pro Pro Ala Val Pro Gln Ser Phe Gln
            180                 185                 190

Val Ala Leu
        195
```

(2) INFORMATION FOR SEQ ID NO:3:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ala Arg Ile Arg Ala Leu Leu Gly Cys Ile Ile Thr Ser Leu Thr
1               5                   10                  15

Gly Arg Asp Lys Asn Gln Val Glu Gly Glu Val Gln Val Val Ser Thr
                20                  25                  30

Ala Thr Gln Ser Phe Leu Ala Thr Cys Val Asn Gly Val Cys Trp Thr
            35                  40                  45

Val Tyr His Gly Ala Gly Ser Lys Thr Leu Ala Gly Pro Lys Gly Pro
    50                  55                  60

Ile Thr Gln Met Tyr Thr Asn Val Asp Gln Asp Leu Val Gly Trp Gln
65                  70                  75                  80

Ala Pro Pro Gly Ala Arg Ser Leu Thr Pro Cys Thr Cys Gly Ser Ser
                85                  90                  95

Asp Leu Tyr Leu Val Thr Arg His Ala Asp Val Ile Pro Val Arg Arg
            100                 105                 110

Arg Gly Asp Ser Arg Gly Ser Leu Leu Ser Pro Arg Pro Val Ser Tyr
    115                 120                 125

Leu Lys Gly Ser Ser Gly Gly Pro Leu Leu Cys Pro Ser Gly His Ala
    130                 135                 140

Val Gly Ile Phe Arg Ala Ala Val Cys Thr Arg Gly Val Ala Lys Ala
145                 150                 155                 160

Val Asp Phe Val Pro Val Glu Ser Met Glu Thr Thr Met Arg
                165                 170
```

(2) INFORMATION FOR SEQ ID NO:4:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Pro Ile Thr Ala Tyr Ser Gln Gln Thr Arg Gly Leu Leu Gly
1               5                   10                  15
```

```
Cys Ile Ile Thr Ser Leu Thr Gly Arg Asp Lys Asn Gln Val Glu Gly
             20                  25                  30

Glu Val Gln Val Val Ser Thr Ala Thr Gln Ser Phe Leu Ala Thr Cys
         35                  40                  45

Val Asn Gly Val Cys Trp Thr Val Tyr His Gly Ala Gly Ser Lys Thr
 50                  55                  60

Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                 85                  90                  95

Pro Cys Thr Cys Gly Ser Ser Asp Leu Tyr Leu Val Thr Arg His Ala
             100                 105                 110

Asp Val Ile Pro Val Arg Arg Arg Gly Asp Ser Arg Gly Ser Leu Leu
             115                 120                 125

Ser Pro Arg Pro Val Ser Tyr Leu Lys Gly Ser Ser Gly Gly Pro Leu
             130                 135                 140

Leu Cys Pro Ser Gly His Ala Val Gly Ile Phe Arg Ala Ala Val Cys
 145                 150                 155                 160

Thr Arg Gly Val Ala Lys Ala Val Asp Phe Val Pro Val Glu Ser Met
                 165                 170                 175

Glu Thr Thr Met Arg
             180

(2) INFORMATION FOR SEQ ID NO:5:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Gln Gln Thr Arg Gly Leu Leu Gly Cys Ile Ile Thr Ser Leu Thr
 1               5                  10                  15

Gly Arg Asp Lys Asn Gln Val Glu Gly Val Gln Val Val Ser Thr
             20                  25                  30

Ala Thr Gln Ser Phe Leu Ala Thr Cys Val Asn Gly Val Cys Trp Thr
             35                  40                  45

Val Tyr His Gly Ala Gly Ser Lys Thr Leu Ala Gly Pro Lys Gly Pro
 50                  55                  60

Ile Thr Gln Met Tyr Thr Asn Val Asp Gln Asp Leu Val Gly Trp Gln
 65                  70                  75                  80

Ala Pro Pro Gly Ala Arg Ser Leu Thr Pro Cys Thr Cys Gly Ser Ser
                 85                  90                  95

Asp Leu Tyr Leu Val Thr Arg His Ala Asp Val Ile Pro Val Arg Arg
             100                 105                 110

Arg Gly Asp Ser Arg Gly Ser Leu Leu Ser Pro Arg Pro Val Ser Tyr
             115                 120                 125

Leu Lys Gly Ser Ser Gly Gly Pro Leu Leu Cys Pro Ser Gly His Ala
             130                 135                 140

Val Gly Ile Phe Arg Ala Ala Val Cys Thr Arg Gly Val Ala Lys Ala
 145                 150                 155                 160

Val Asp Phe Val Pro Val Glu Ser Met Glu Thr Thr Met Arg
                 165                 170
```

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Gly Ser Val Val Ile Val Gly Arg Ile Ile Leu Ser Gly Arg
1               5                   10
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Fmoc-Tyr"

(xi) SEQUENCE DESCRIPTION: SEQ ID NO:7:

```
Xaa Gln Glu Phe Asp Glu Met Glu Glu Cys Ala Ser His Leu Pro Tyr
1               5                   10                  15
Ile Glu Gln Gly
            20
```

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Tyr"

(xi) SEQUENCE DESCRIPTION: SEQ ID NO:8:

```
Xaa Gln Glu Phe Asp Glu Met Glu Glu Cys Ala Ser His Leu Pro Tyr
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Tyr"

(xi) SEQUENCE DESCRIPTION: SEQ ID NO:9:

```
Xaa Gln Glu Phe Asp Glu Met Glu Glu Cys Ala Ser His Leu Pro
1               5                   10                  15
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Tyr"

(xi) SEQUENCE DESCRIPTION: SEQ ID NO:10:

```
Xaa Gln Glu Phe Asp Glu Met Glu Glu Cys Ala Ser His Leu
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Tyr"

(xi) SEQUENCE DESCRIPTION: SEQ ID NO:11:

```
Xaa Gln Glu Phe Asp Glu Met Glu Glu Cys Ala Ser His
1               5                   10
```

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Tyr"

(xi) SEQUENCE DESCRIPTION: SEQ ID NO:12:

```
Xaa Gln Glu Phe Asp Glu Met Glu Glu Cys Ala Ser
1               5                   10
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1
            (D) OTHER INFORMATION: /note= "Xaa is Ac-Tyr"

(xi) SEQUENCE DESCRIPTION: SEQ ID NO:13:

Xaa Gln Glu Phe Asp Glu Met Glu Glu Cys Ala
1               5                   10

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:14:

Xaa Glu Met Glu Glu Cys Ala Ser His Leu Pro Tyr
1               5                   10

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Glu"

(xi) SEQUENCE DESCRIPTION: SEQ ID NO:15:

Xaa Met Glu Glu Cys Ala Ser His Leu Pro
1               5                   10

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Met"

(xi) SEQUENCE DESCRIPTION: SEQ ID NO:16:

Xaa Glu Glu Cys Ala Ser His Leu
1               5

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Glu"

(xi) SEQUENCE DESCRIPTION: SEQ ID NO:17:

Xaa Cys Ala Ser His Leu Pro Tyr Ile Glu Gln Gly
1               5                   10

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:18:

Xaa Glu Met Glu Glu Cys Ala Ser His Leu
1               5                   10

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Asp Glu Met Glu Glu Cys Ala Ser His Leu
1               5                   10

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Fmoc-Asp"

(xi) SEQUENCE DESCRIPTION: SEQ ID NO:20:

Xaa Glu Met Glu Glu Cys Ala Ser His Leu
1               5                   10

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: single
        (D) TOPOLOGY: linear

```
      (ii) MOLECULE TYPE: peptide (ix) FEATURE:
           (A) NAME/KEY: Peptide
           (B) LOCATION: 1
           (D) OTHER INFORMATION: /note= "Xaa is Ac-Asp"

(xi) SEQUENCE DESCRIPTION: SEQ ID NO:21:

Xaa Cys Ser Thr Pro Cys Ser Gly Ser Val
1               5                   10

(2) INFORMATION FOR SEQ ID NO:22:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Peptide
           (B) LOCATION: 1
           (D) OTHER INFORMATION: /note= "Xaa is Ac-Glu"

(xi) SEQUENCE DESCRIPTION: SEQ ID NO:22:

Xaa Asp Val Val Cys Cys Ser Met Ser Tyr
1               5                   10

(2) INFORMATION FOR SEQ ID NO:23:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Peptide
           (B) LOCATION: 1
           (D) OTHER INFORMATION: /note= "Xaa is Ac-Ala"

(xi) SEQUENCE DESCRIPTION: SEQ ID NO:23:

Xaa Glu Met Glu Glu Cys Ala Ser His Leu
1               5                   10

(2) INFORMATION FOR SEQ ID NO:24:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Peptide
           (B) LOCATION: 1
           (D) OTHER INFORMATION: /note= "Xaa is Ac-Asp"

(xi) SEQUENCE DESCRIPTION: SEQ ID NO:24:

Xaa Ala Met Glu Glu Cys Ala Ser His Leu
1               5                   10

(2) INFORMATION FOR SEQ ID NO:25:
```

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:25:

Xaa Glu Ala Glu Glu Cys Ala Ser His Leu
1               5                   10

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:26:

Xaa Glu Met Ala Glu Cys Ala Ser His Leu
1               5                   10

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:27:

Xaa Glu Met Glu Ala Cys Ala Ser His Leu
1               5                   10

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:28:

Xaa Glu Met Glu Glu Ala Ala Ser His Leu
```

```
1               5                   10
```

(2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:29:

```
Xaa Glu Met Glu Glu Cys Ala Ala His Leu
1               5                   10
```

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: 1
        (D) OTHER INFORMATION: /note= "Xaa is Ac-Asp"

(xi) SEQUENCE DESCRIPTION: SEQ ID NO:30:

```
Xaa Glu Met Glu Glu Cys Ala Ser Ala Leu
1               5                   10
```

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:31:

```
Xaa Glu Met Glu Glu Cys Ala Ser His Ala
1               5                   10
```

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1

(D) OTHER INFORMATION: /note= "Xaa is Ac-Glu"

(xi) SEQUENCE DESCRIPTION: SEQ ID NO:32:

Xaa Glu Met Glu Glu Cys Ala Ser His Leu
1               5                   10

(2) INFORMATION FOR SEQ ID NO:33:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1
              (D) OTHER INFORMATION: /note= "Xaa is Ac-Asn"

(xi) SEQUENCE DESCRIPTION: SEQ ID NO:33:

Xaa Glu Met Glu Glu Cys Ala Ser His Leu
1               5                   10

(2) INFORMATION FOR SEQ ID NO:34:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1
              (D) OTHER INFORMATION: /note= "Xaa is Ac-Lys"

(xi) SEQUENCE DESCRIPTION: SEQ ID NO:34:

Xaa Glu Met Glu Glu Cys Ala Ser His Leu
1               5                   10

(2) INFORMATION FOR SEQ ID NO:35:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1
              (D) OTHER INFORMATION: /note= "Xaa is Ac-Asp"

(xi) SEQUENCE DESCRIPTION: SEQ ID NO:35:

Xaa Glu Met Glu Glu Cys Ser Ser His Leu
1               5                   10

(2) INFORMATION FOR SEQ ID NO:36:

(i) SEQUENCE CHARACTERISTICS:
              (A) LENGTH: 10 amino acids
              (B) TYPE: amino acid
              (C) STRANDEDNESS: single
              (D) TOPOLOGY: linear

```
       (ii) MOLECULE TYPE: peptide (ix) FEATURE:
            (A) NAME/KEY: Peptide
            (B) LOCATION: 1
            (D) OTHER INFORMATION: /note= "Xaa is Ac-Asp"

(xi) SEQUENCE DESCRIPTION: SEQ ID NO:36:

Xaa Glu Met Glu Glu Cys Phe Ser His Leu
1               5                   10

(2) INFORMATION FOR SEQ ID NO:37:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa is Ac-Asp"

(ix) FEATURE:
            (A) NAME/KEY: Peptide
            (B) LOCATION: 6
            (D) OTHER INFORMATION: /note= "Xaa is Alg (alylglycine)"

(xi) SEQUENCE DESCRIPTION: SEQ ID NO:37:

Xaa Glu Met Glu Glu Xaa Ala Ser His Leu
1               5                   10

(2) INFORMATION FOR SEQ ID NO:38:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa is Ac-Asp"

(ix) FEATURE:
            (A) NAME/KEY: Peptide
            (B) LOCATION: 6
            (D) OTHER INFORMATION: /note= "Xaa is Abu (2-aminobutyric
                  acid)"

(xi) SEQUENCE DESCRIPTION: SEQ ID NO:38:

Xaa Glu Met Glu Glu Xaa Ala Ser His Leu
1               5                   10

(2) INFORMATION FOR SEQ ID NO:39:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
```

(D) OTHER INFORMATION: /note= "Xaa is Ac-Asp"

(xi) SEQUENCE DESCRIPTION: SEQ ID NO:39:

Xaa Glu Met Glu Glu Thr Ala Ser His Leu
1               5                   10

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 6
        (D) OTHER INFORMATION: /note= "Xaa is Nva (norvaline)"

(xi) SEQUENCE DESCRIPTION: SEQ ID NO:40:

Xaa Glu Met Glu Glu Xaa Ala Ser His Leu
1               5                   10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(xi) SEQUENCE DESCRIPTION: SEQ ID NO:41:

Xaa Glu Met Glu Glu Val Ala Ser His Leu
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 6
        (D) OTHER INFORMATION: /note= "Xaa is Abu (2-amminobutyric
                acid) ester bonded to the following residue"

(ix) FEATURE:
        (A) NAME/KEY: Peptide
        (B) LOCATION: 7

```
        (D) OTHER INFORMATION: /note= "Xaa is Ala ester bonded to
            the adjacent preceding residue"

(ix) FEATURE:
        (A) NAME/KEY: Peptide
        (B) LOCATION: 13
        (D) OTHER INFORMATION: /note= "Xaa is Lys (N(-Ac)-NH2"

(xi) SEQUENCE DESCRIPTION: SEQ ID NO:42:

Xaa Glu Met Glu Glu Xaa Xaa Ser His Leu Pro Tyr Xaa
1               5                   10

(2) INFORMATION FOR SEQ ID NO:43:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 6
        (D) OTHER INFORMATION: /note= "Xaa is Thr ester bonded to
            the adjacent following residue"

(ix) FEATURE:
        (A) NAME/KEY: Peptide
        (B) LOCATION: 7
        (D) OTHER INFORMATION: /note= "Xaa is Ala ester bonded to
            the adjacent preceding residue"

(ix) FEATURE:
        (A) NAME/KEY: Peptide
        (B) LOCATION: 13
        (D) OTHER INFORMATION: /note= "Xaa is Lys(N(-Ac)-NH2"

(xi) SEQUENCE DESCRIPTION: SEQ ID NO:43:

Xaa Glu Met Glu Glu Xaa Xaa Ser His Leu Pro Tyr Xaa
1               5                   10

(2) INFORMATION FOR SEQ ID NO:44:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 6
        (D) OTHER INFORMATION: /note= "Xaa is Abu (2-amminobutyric
            acid) ester bonded to the adjacent following residue"

(ix) FEATURE:
        (A) NAME/KEY: Peptide
        (B) LOCATION: 7
        (D) OTHER INFORMATION: /note= "Xaa is Ala ester bonded to
            the adjacent preceding residue"
```

```
     (ix) FEATURE:
           (A) NAME/KEY: Peptide
           (B) LOCATION: 13
           (D) OTHER INFORMATION: /note= "Xaa is
                Lys(N(-[3H])-CH3CO)-NH2"

(xi) SEQUENCE DESCRIPTION: SEQ ID NO:44:

Xaa Glu Met Glu Glu Xaa Xaa Ser His Leu Pro Tyr Xaa
1               5                   10

(2) INFORMATION FOR SEQ ID NO:45:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Peptide
           (B) LOCATION: 1
           (D) OTHER INFORMATION: /note= "Xaa is Ac-Asp"

(ix) FEATURE:
           (A) NAME/KEY: Peptide
           (B) LOCATION: 3
           (D) OTHER INFORMATION: /note= "Xaa is Asp (EDANS)"

(ix) FEATURE:
           (A) NAME/KEY: Peptide
           (B) LOCATION: 6
           (D) OTHER INFORMATION: /note= "Xaa is Abu (2-amminobutyric
                acid) ester bonded to the following residue"

(ix) FEATURE:
           (A) NAME/KEY: Peptide
           (B) LOCATION: 7
           (D) OTHER INFORMATION: /note= "Xaa is Ala ester bonded to
                the adjacent preceding residue"

(ix) FEATURE:
           (A) NAME/KEY: Peptide
           (B) LOCATION: 9
           (D) OTHER INFORMATION: /note= "Xaa is Lys (DABCYL)"

(xi) SEQUENCE DESCRIPTION: SEQ ID NO:45:

Xaa Glu Xaa Glu Glu Xaa Xaa Ser Xaa
1               5

(2) INFORMATION FOR SEQ ID NO:46:

(i) SEQUENCE CHARACTERISTICS:
           (A) LENGTH: 9 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Peptide
           (B) LOCATION: 1
           (D) OTHER INFORMATION: /note= "Xaa is Ac-Asp"

(ix) FEATURE:
           (A) NAME/KEY: Peptide
           (B) LOCATION: 2
           (D) OTHER INFORMATION: /note= "Xaa is Asp (EDANS)"

(ix) FEATURE:
           (A) NAME/KEY: Peptide
           (B) LOCATION: 6
           (D) OTHER INFORMATION: /note= "Xaa is Abu (2-amminobutyric
``` acid) ester bonded to the following residue"

(ix) FEATURE:
        (A) NAME/KEY: Peptide
        (B) LOCATION: 7
        (D) OTHER INFORMATION: /note= "Xaa is Ala ester bonded to
            the adjacent preceding residue"

(ix) FEATURE:
        (A) NAME/KEY: Peptide
        (B) LOCATION: 9
        (D) OTHER INFORMATION: /note= "Xaa is Lys (DABCYL)"

(xi) SEQUENCE DESCRIPTION: SEQ ID NO:46:

Xaa Xaa Met Glu Glu Xaa Xaa Ser Xaa
1               5

(2) INFORMATION FOR SEQ ID NO:47:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 13
        (D) OTHER INFORMATION: /note= "Xaa is Lys-(-(3H)Ac"

(xi) SEQUENCE DESCRIPTION: SEQ ID NO:47:

Xaa Glu Met Glu Glu Cys Ala Ser His Leu Pro Tyr Xaa
1               5                   10

(2) INFORMATION FOR SEQ ID NO:48:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Met Ala Pro Ile Thr Ala Tyr Ser Gln Gln Thr
1               5                   10

(2) INFORMATION FOR SEQ ID NO:49:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa is Ac-Asp"

(ix) FEATURE:
        (A) NAME/KEY: Peptide
        (B) LOCATION: 6

-continued

```
            (D) OTHER INFORMATION: /note= "Xaa is Abu-OH"

(xi) SEQUENCE DESCRIPTION: SEQ ID NO:49:

Xaa Glu Met Glu Glu Xaa
1               5

(2) INFORMATION FOR SEQ ID NO:50:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1
            (D) OTHER INFORMATION: /note= "Xaa is HO-CH(CH3)CO"

(ix) FEATURE:
            (A) NAME/KEY: Peptide
            (B) LOCATION: 7
            (D) OTHER INFORMATION: /note= "Xaa is Lys(Nn-[3H]-CH3CO)-NH2"

(xi) SEQUENCE DESCRIPTION: SEQ ID NO:50:

Xaa Ser His Leu Pro Tyr Xaa
1               5
```

METHODOLOGY TO PRODUCE, AND PURIFY AND ASSAY POLYPEPTIDES WITH THE PROTEOLYTIC ACTIVITY OF THE HCV NS3 PROTEASE

DESCRIPTION

The present invention relates to molecular biology and to hepatitis C virus (HCV) virology. More specifically, the invention has as its subject a process for producing, in a pure form and in high quantities, polypeptides having the proteolytic activity of HCV NS3 protease, and a method for the effective reproduction in vitro of the proteolytic activity of these polypeptides in order to define an enzymatic assay capable of selecting, for therapeutic purposes, compounds inhibiting the enzyme activity associated with NS3.

As is known, the hepatitis C virus (HCV) is the main etiological agent of non-A, non-B hepatitis (NANB). It is estimated that HCV causes at least 90% of post-transfusional NANB viral hepatitis and 50% of sporadic NANB hepatitis. Although great progress has been made in the selection of blood donors and in the immunological characterisation of blood used for transfusions, there is still a high number of HCV infections among recipients of blood transfusions (one million or more infections every year throughout the world). Approximately 50% of HCV-infected individuals develop liver cirrhosis within a period that can range from 5 to 40 years. Furthermore, recent clinical studies suggest that there is a correlation between chronic HCV infection and the development of hepatocellular carcinoma.

HCV is an enveloped virus containing an RNA positive genome of approximately 9.4 kb. This virus is a member of the Flaviviridae family, the other members of which are the flaviviruses and the pestiviruses.

The RNA genome of HCV has recently been mapped. Comparison of sequences from the HCV genomes isolated in various parts of the-world has shown that these sequences can be extremely heterogeneous. The majority of the HCV genome is occupied by an open reading frame (ORF) that can vary between 9030 and 9099 nucleotides. This ORF codes for a single viral polyprotein, the length of which can vary from 3010 to 3033 amino acids. During the viral infection cycle, the polyprotein is proteolytically processed into the individual gene products necessary for replication of the virus.

The genes coding for HCV structural proteins are located at the 5'-end of the ORF, whereas the region coding for the non-structural proteins occupies the rest of the ORF.

The structural proteins consist of C (core, 21 kDa), E1 (envelope, gp37) and E2 (NS1, gp61). C is a non-glycosylated protein of 21 kDa which probably forms the viral nucleocapsid. The protein E1 is a glycoprotein of approximately 37 kDa, which is believed to be a structural protein for the outer viral envelope. E2, another membrane glycoprotein of 61 kDa, is probably a second structural protein in the outer envelope of the virus.

The non-structural region starts with NS2 (p24), a hydrophobic protein of 24 kDa whose function is unknown.

NS3, a protein of 68 kDa which follows NS2 in the polyprotein, is predicted to have two functional domains: a serine protease domain within the first 200 amino-terminal amino acids, and an RNA-dependent ATPase domain at the carboxy terminus.

The NS4 gene region codes for NS4A (p6) and NS4B (p26), two hydrophobic proteins of 6 and 26 kDa, respectively, whose functions have not yet been fully clarified.

The NS5 gene region also codes for two proteins, NS5A (p56) and NS5B (p65), of 56 and 65 kDa, respectively. Amino acid sequences present in all the RNA-dependent RNA polymerases can be recognised within the NS5 region. This suggests that the NS5 region contains components of the viral replication machinery.

Various molecular biological studies indicate that the signal peptidase, a protease associated with the endoplasmic reticulum of the host cell, is responsible for proteolytic processing in the non-structural region, that is to say at sites C/E1, E1/E2 and E2/NS2.

The serine protease in NS3 is responsible for cleavage at the junctions between NS3 and NS4A, between NS4A and NS4B, between NS4B and NS5A and between NS5A and NS5B. In particular it has been found that the cleavage made by this serine protease leaves a cysteine or a treonine residue on the amino-terminal side (position P1) and an alanine or serine residue on the carboxy-terminal side (position P1') of the cleavage site. It has been shown that the protease contained in NS3 is a heterodimeric protein in vivo, forming a complex with the protein NS4A. Formation of this complex increases proteolytic activity on sites NS4A/NS4B and NS5A/NS5B, and is a necessary requisite for proteolytic processing of site NS4B/NS5A.

A second protease activity of HCV appears to be responsible for the cleavage between NS2 and NS3. This protease activity is contained in a region comprising both part of NS2 and the portion of NS3 containing the serine protease domain, but does not use the same catalytic mechanism as the latter.

A substance capable of interfering with the proteolytic activity associated with the protein NS3 might constitute a new therapeutic agent. In effect, inhibition of this protease activity would involve stopping the proteolytic processing of the non-structural region of the HCV polyprotein and, consequently, would prevent viral replication of the infected cells.

This sequence of events has been verified for the homologous flavivirus, which, unlike HCV, infects cell line cultures. In this case, it has been shown that genetic manipulations involving generation of a protease no longer capable of carrying out its catalytic activity, abolishes the ability of the virus to replicate (1).

Furthermore, it has been widely shown, both in vitro and in clinical studies, that compounds capable of interfering with the HIV protease activity are capable of inhibiting replication of this virus (2).

The methods used to generate molecules with therapeutic potential are known to those operating in this field. Generally speaking, collections of compounds containing a large number of single chemical entities with a high molecular diversity are made to undergo an automatised assay in order to identify single active agents, which then undergo further chemical modifications in order to improve their therapeutic potential. Other approaches may include rational modification of substrates or ligands of specific target protein, with the aim of developing high binding affinity compounds capable of altering or abolishing the biological activity of the protein under examination. Determination of the three-dimensional structure of a target protein, by means of methods known in the sector as X-ray crystallography or nuclear magnetic resonance (NMR) allows rational design of molecules capable of binding specifically to the protein and which, as a result of this, have the ability to interfere with the biological properties of that protein.

Research on compounds capable of interfering with the biological activity of the protease contained in the hepatitis C virus NS3 protein is hampered by the difficulty in producing sufficient amounts of purified protein with unaltered catalytic properties, and by the need to use co-factors to enhance the activity of the enzyme in vitro.

There is therefore a need in the specific field for a process to produce NS3, or similar products, in larger amounts that has been possible in the past, and with an in vitro activity sufficient to select inhibitors.

The present invention consists of isolated and purified polypeptides, with the proteolytic activity of the HCV protein NS3, characterised by the fact that they have an amino acid sequence chosen from among the sequences SEQ ID NO:1, SEQ ID NO:2, SEQ ID NO:3, SEQ ID NO:4 and SEQ ID NO:5.

The invention also comprises expression vectors—to produce the polypeptides represented by sequences SEQ ID NO:1, SEQ ID NO:2, SEQ ID NO:3, SEQ ID NO:4 and SEQ ID NO:5 which have the proteolytic activity of HCV NS3—comprising:

a polynucleotide coding for one of said polypeptides;

functional regulation, transcription and translation sequences in said host cell, operatively bonded to said polynucleotide coding for one of said polypeptides; and optionally, a selectable marker.

The invention also extends to a host cell, either eukaryotic or prokaryotic, transformed using an expression vector containing a DNA sequence coding for SEQ ID NO:1, SEQ ID NO:2, SEQ ID NO:3, SEQ ID NO:4 and SEQ ID NO:5 in such a way as to allow said host cell to express the specific coded polypeptide in the chosen sequence. The invention further comprises a process for preparation of polypeptides with sequence selected from the group comprising SEQ ID NO:1, SEQ ID NO:2, SEQ ID NO:3, SEQ ID NO:4 and SEQ ID NO:5, characterised by the fact that it comprises, in combination, the following operations:

transformation of a host cell, either eukaryotic or prokaryotic, using one of the expression vectors mentioned above; and expression of the desired nucleotide sequence to produce the chosen polypeptide; and purification of the polypeptide thus obtained, avoiding resolubilisation protocols.

The present invention also has as its object a method for reproducing in vitro the proteolytic activity of the HCV NS3 protease, characterised by the fact that the activity of purified polypeptides, with sequences chosen from the group comprising SEQ ID NO:1, SEQ ID NO:2, SEQ ID NO:3, SEQ ID NO:4 and SEQ ID NO:5, similar to NS3, is reproduced in a solution containing 30–70 mM Tris pH 6.5–8.5, 3–30 mM dithiothreitol (DTT), 0.5–3% 3-[(3-colammide-propyl)-dimethyl-ammonium]-1-propansulphonate (CHAPS) and 30–70% glycerol at temperatures of between 20 and 25° C. and by the fact that in these conditions the activity of the above mentioned polypeptides can be kinetically determined and quantified on peptide substrates even in the absence of co-factors.

An assay of the protease activity of the polypeptides SEQ ID NO:1, SEQ ID NO:2, SEQ ID NO:3, SEQ ID NO:4 and SEQ ID NO:5 can be performed by cleaving a substrate providing detectable products. The cleavage is preferably detected using methods based on radioactive, colorimetric or fluorimetric signals. Methods such as HPLC and the like are also suitable. According to the present invention, the substrates used are synthetic peptides corresponding to the HCV polyprotein NS4A/4B junction. If necessary, peptides containing the amino acid sequence SEQ ID NO:6, or parts thereof, can be used as co-factor of the NS3 protease.

Peptides suitable for use as substrates are the peptide represented by the sequence SEQ ID NO:7 and derivatives thereof with N and/or C-terminal deletions (SEQ ID NOS:8–12, 14, 18–20) and the peptide represented by the sequence SEQ ID NO:47. Particularly suitable are the decapeptides represented by the sequences SEQ ID NOS:18–20, especially SEQ IS NO:18 and the sequences derived therefrom SEQ ID NOS:29–32, 35.

These peptides can be used for a high-throughput assay of NS3 protease activity at a concentration of the latter of between 100–200 nM.

According to the invention depsipeptide substrates (peptides with at least one ester bond in the sequences) can also be used advantageously for a high-throughput assay of the activity of the NS3 protease. It is, in fact, known that it is desirable to run the assay at the lowest possible enzyme concentration compatible with sufficient substrate conversion. This maximises sensitivity to inhibition and allows to screen for inhibitors which are present at very low concentrations in compound mixtures or combinatorial libraries. Substrates for NS3 protease with a standard amide at the scissile bond between residues P1 and P1' have $K_{cat}/K_m$ values between 30–100 $M^{-1}$ $s^{-1}$. This sets a practical range of enzyme concentration for a high-throughput assay of 100–200 nM. To lower this concentration it is necessary to use substrates with higher $K_{cat}/K_m$ values. Substrates containing an ester bond between P1 and P1' are ideally suited for this, since formation of the acyl-enzyme intermediate is accomplished much more readily due to the more thermodynamically favourable transesterification reaction (8). The depsipeptide substrates according to the invention have very high $K_{cat}/K_m$ values, and this brings the useful range of NS3 concentration in the high-throughput assay to 0.5–2 nM. These substrates may be synthesised in high yield on solid-phase by standard chemical methodology.

Conventional assays are suitable for high throughput screening, but they require hydrolysis of at least 10% of the substrate before the product can be detected conveniently. This precludes determination of true initial rates, which are important for accurate kinetic studies. To overcome these difficulties, an assay has been developed that allows continuous monitoring of protease activity. The assay relies on specially tailored synthetic substrates, which are capable of direct-, continuous signal generation that is directly proportional to the extent of substrate hydrolysis, thus avoiding the need for separation of the substrate from the reaction product. The depsipeptides used (SEQ ID NOS:45 and 46), the chemical formulas of which are given in FIG. 12, are internally quenched fluorogenic substrates based on resonance energy transfer (RET). They contain a fluorescent donor, 5-[(2'-aminoethyl)amino]naphthalenesulfonic acid (EDANS), near one end of the peptide, and an acceptor group, 4-[[4'-(dimethylamino)phenyl]azo]benzoic acid (DABCYL) near the other end. The fluorescence of this type of substrate is initially quenched by intramolecular RET between the donor and the acceptor, but as the enzyme cleaves the substrate the fluorescence increases. EDANS and DABCYL were selected as donor/acceptor pair because of the excellent spectral overlap between the fluorescent emission of the former and the absorption of the latter (13–17). RET efficiency depends on the distance between the donor and the acceptor, i.e. the closer the two, the higher the quenching. For the EDANS/DABCYL couple, the Förster distance for 50% energy-transfer ($R_0$) is 33 Å. The maximum distance between EDANS/DABCYL reported in a substrate is 11 amino acids (19) which, assuming an extended conformation for the peptide, corresponds to R=39.8 Å, with a calculated RET efficiency of 24.5%. This corresponds to a 10-fold increase in fluorescence upon substrate cleavage.

Up to this point a general description has been given of the present invention. With the aid of the following examples, a more detailed description of specific embodiments thereof will now be given, in order to give a better understanding of the aims, characteristics, advantages and operation methods of the invention.

FIGS. 2A and 2B show the plasmid vectors for transfer and expression in *E. coli* of the polypeptides represented by sequences SEQ ID NO:2, SEQ ID NO:3, SEQ ID NO:4 and SEQ ID NO:5, respectively.

FIG. 12 shows the chemical formula of the depsipeptide substrates (SEQ ID NO:45 and SEQ2 ID NO:46) for a continuous assay of NS3 activity based on RET intramolecular fluorescence quenching.

EXAMPLE 1

Method of Expression of HCV NS3 Protease in *Spodoptera frugiperda* Clone 9 Cultured Cells Systems for expression of foreign genes in insect cultured cells, such as *Spodoptera frugiperda* clone 9 (Sf9) cells infected with baculovirus vectors are known in the art (3). Heterologous genes are usually placed under the control of the strong polyhedrin promoter of the *Autographa californica* nuclear polyhedrosis virus or the *Bombix mori* nuclear polyhedrosis virus. Methods for the introduction of heterologous DNA in the desired site in the baculoviral vectors by homologous recombination are also known in the art (4).

Figure 1:
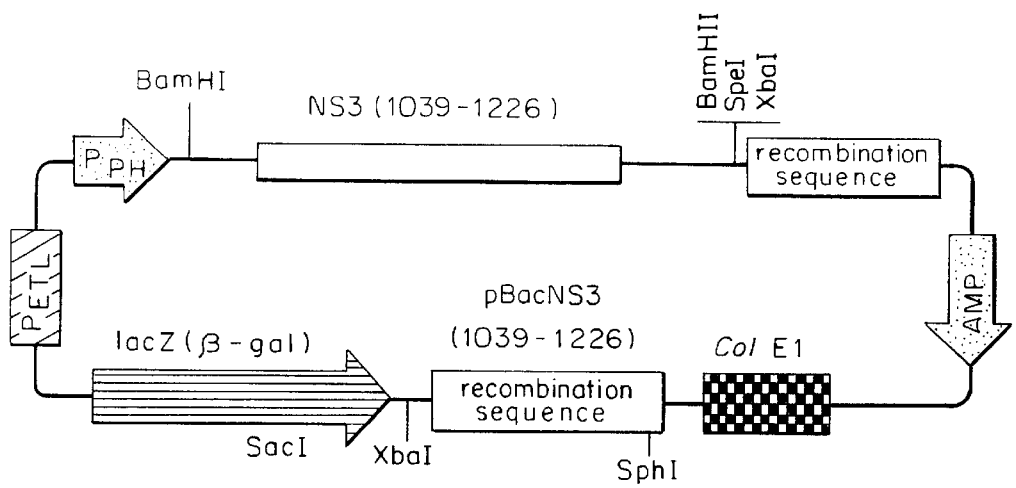
FIG. 1 shows the plasmid vector used for transfer and expression of the polypeptide represented by SEQ ID No:1 in Spodoptera frugiperda clone 9 cells.

The plasmid vector pBacNS3 (1039–1226) is a derivative of pBlueBacIII (Invitrogen) and was constructed for transfer of a gene coding for a polypeptide with the activity of NS3 (1039–1226). For this purpose, the nucleotide sequence coding for this polypeptide described in SEQ ID NO:1 was obtained by PCR using oligonucleotides that insert an ATG condon at 5' and a TAG stop codon at 3' in the sequence. The fragment obtained in this way was inserted at the BamH1 site of the vector pBlueBacIII, following treatment with the Klenow DNA polymerase fragment. The plasmid is illustrated in FIG. 1.

*Spodoptera frugiperda* clone 9 (Sf9) cells and baculovirus recombination kits were purchased from Invitrogen. Cells were grown on dishes or in suspension at 27° C. in complete Grace's insect medium (Gibco) containing 10% foetal bovine serum (Gibco). Transfection, recombination, and selection of baculovirus constructs were performed as recommended by the manufacturer.

For protein expression, Sf9 cells were infected with the recombinant baculovirus at a density of $2\times10^6$ cells per ml in a ratio of about 5 virus particles per cell. The cells were cultivated in suspension for 72 hours at 23° C. Lowering the temperature from 27° C., which corresponds normally to the optimal growth temperature, to 23° C. is crucial in order to obtain a soluble and active protein.

After harvesting the cells by centrifugation and washing them with PBS (20 mM sodium phosphate pH 7.4, 140 mM NaCl) the pellet was re-suspended in 25 mM sodium phosphate pH 6.5, 20-% glycerol, 0.5% 3-[(3-colammide-propyl)-dimethyl-ammonium]-1-propansulphonate (CHAPS), 10 mM dithiothreitol (DTT), 1 mM ethylendiammino-tetracetic acid (EDTA). The cells were destroyed at 4° C. by means of four cycles of sonication at 10 W with a duration of 30 seconds each, using a Branson 250 instrument. The homogenate obtained in this way was pelleted by centrifugation at 120,000×g for one hour and the supernatant was loaded onto an HR26/10 S-Sepharose column (Pharmacia) balanced with 25 mM sodium phosphate pH 6.5, 10% glycerol, 2 mN DTT, 1 mM EDTA, 0.1% CHAPS at a flow rate of 2 ml/min. After washing with two volumes of column the protease was eluted with an NaCl gradient between 0 and 1 M. The fractions-containing the protease were identified using Western blotting methodology with NS3-specific polyclonal antibodies, concentrated to 3 ml using an Amicon ultrafiltration cell equipped with a Ym10 membrane and chromatographed onto a Superdex 75 HR26/60 column (Pharmacia) equilibrated with 50 mM sodium phosphate pH 7.5, 10% glycerol, 2 mM DTT, 0.1% CHAPS, 1 mM ESTA and a flow rate of 1 ml/min. The fractions containing the protease were pooled and underwent further chromatography on a Mono-S HR5/5 column (Pharmacia) equilibrated with the same buffer used in the previous column. The protease was eluted in a pure form from this column, applying a linear NaCl gradient between 0 and 0.5 M. The protease was stored at −80° C. in 50% glycerol, 0.5% CHAPS, 10 mM DTT and 50 mM sodium phosphate pH 7.5. The yield of the process is 0.5 mg/l of cells. The purified protein has a catalytic activity $K_{cat}/K_m$ 120–200 M-1 s-1 measured in 50 mM Tris pH 7.5, 50% glycerol, 2% CHAPS, 30 mM DTT at 23° C. using the peptide substrate Fmoc-Tyr-Gln-Glu-Phe-Asp-Glu-Met-Glu-Glu-Cys-Ala-Ser-His-Leu-Pro-Tyr-Ile-Glu-Gln-Gly (SEQ ID NO:7), derived from the polyprotein cleavage site between NS4A and NS4B. The cleavage products deriving from this reaction were separated using HPLC, isolated and identified by mass spectrometry, confirming that proteolytic cleavage took place between cysteine and alanine. The concentration of protease necessary to determine activity was between 100 nM and 1.6 µM.

EXAMPLE 2

Method or Expression of HCV NS3 Protease in *E. coli*

The plasmids pT7-7(NS3 1039–1226), pT7-7 (NS3 1039–1206), pT7-7 (NS3 1027–1206) and pT7-7 (NS3 1033–1206), described in FIGS. 2A and 2B, were constructed in order to allow expression in *E. coli* of the polypeptides indicated in SEQ ID NO:2 and SEQ ID NO:3, and SEQ ID NO:4 and SEQ ID NO:5, respectively. The protein fragments contain variants of the protease domain of the HCV NS3 protein. The respective fragments of HCV cDNA were cloned downstream of the bacteriophage T7 Ø10 promoter and in frame with the first ATG codon of the phage T7 gene 10 protein, using methods that are known to the practice. The pT7-7 plasmids containing NS3 sequences also contains the gene for the β-lactamase enzyme that can be used as a marker of a selection of *E. coli* cells transformed with these plasmids.

The plasmids were then transformed in the *E. coli* strain BL21(DE53), which is normally employed for high-level expression of genes cloned into expression vectors containing the T7 promoter. In this strain of *E. coli*, the T7 polymerase gene is carried on the bacteriophage λ DE53, which is integrated into the chromosome of BL21 cells (5). Expression from the gene of interest is induced by addition of isopropylthiogalactoside (IPTG) to the growth medium according to a procedure that has been previously described (5). Over 90% of the proteins expressed using one of the plasmids mentioned above is found in an insoluble form in inclusion bodies, from which it i s possible to obtain a soluble and active protein following refolding methods known to the field (see for example (6)). Refolding protocols have often variable yields of catalytically active protein, and they require extremely controlled conditions, or cause irreversible modifications of the protein (such as carbamylation in the presence of urea), or require impractical procedures, such as the use of extremely diluted protein solutions, or dialysis of exceedingly large volumes of samples.

To avoid these problems, a method has been developed, which is described below, for the production of the HCV protease in a soluble and active form, avoiding thus resolubilisation protocols: *E. coli* BL21 (DE-53) transformed using one of the plasmids mentioned above were grown at 37° C. until reaching a cell density that causes absorption of 0.8 OD (OD stands for optical density) at 600 nm. At this point the temperature was lowered to 30° C. in 15–20 minutes and 400 µM IPTG was added to induce expression of the protein. The temperature was then lowered further to 22–24° C. within a period of 20–30 minutes. The cultures were stirred for a further 4 hours at this temperature. At this point the cells were harvested by centrifugation and washed using PBS.

Purification Method

The pellets resulting from the operations described above were incubated o n ice for 5 minutes and re-suspended in 25 mM sodium phosphate pH 6.5, 50% glycerol, 0.5% CHAPS, 10 DTT, 1 mM EDTA (buffer A) pre-cooled to 4° C. 10 ml of this buffer was used for each liter of bacterial culture. After a further 5–10 minutes of incubation on ice the cell suspension was homogenised using a French press. The resulting homogenate was centrifuged at 120,000×g. The supernatants from this centrifugation were preserved on ice, whereas the pellets were re-suspended in buffer A (1 ml to each liter of bacteria culture). After the addition of 1 mM MgCl2 and DNaseI, the suspension was incubated for 10 minutes at 20° C. and re-centrifuged for 1 hour at 120,000× g. The supernatant from this second centrifugation was pooled with the first supernatant and the resulting protein solution was adsorbed on S-Sepharose (or SP-Sepharose) resin (Pharmacia) equilibrated with 25 mM sodium phosphate pH 6.5, 10% glycerol, 0.5% CHAPS, 3 mM DTT, 1 mM EDTA (buffer B). 10 ml of resin suspended in 5 ml of buffer B was used for each liter of bacterial culture. The resin was stirred for 1 hour at 4° C., collected by filtration, washed with buffer B and poured into an appropriate chromatography column. The protease was eluted with an NaCl gradient between 0 and 1 M. Fractions containing the protease were identified using Western blotting, pooled and concentrated using Centriprep 10 concentrators (Amicon) until reaching a concentration of 6–10 mg/ml in protein, determined using the BIORAD method. Up to 3 ml of this solution was loaded onto a HR 26/60 Superdex 75 or up to 20 ml was loaded onto an HR 60/600 Superdex 75 (both Pharmacia) equilibrated with 50 mM sodium phosphate pH 7.5, 10% glycerol, 3 mM DTT, 0.5% CHAPS (buffer C) and chromatography was carried out at 1 ml/min (HR26/60) or 5 ml/min (HR60/600). The fractions containing the protease were pooled and further purified by chromatography on HR 5/5 Mono S (Pharmacia) equilibrated with buffer C. The protease was eluted from this column with an NaCl gradient between 0 and 0.5 M. Purification to homogeneity was also possible with the following modification: after elution from S-Sepharose the fractions containing the protease were diluted 1:4 in buffer C and loaded onto Heparin-Sepharose. Elution from this resin was obtained with an NaCl gradient between 0 and 0.5 M. The protein was then chromatographed on hydroxiapatite or Superdex 75 as described above. The yield is 1–2 mg of purified protein per liter of bacterial culture.

Characterisation of the Purified Protein

The purified protein was characterised by means of gel filtration, reverse-phase HPLC, mass spectrometry and N-terminal sequence analysis.

Analytical gel filtration experiments showed that the protein is monomeric. The protein expressed using pT7-7 (NS3 1027–1206) shows three peaks following reverse-phase HPLC chromatography. Mass spectrometry analysis and determination of the N-terminal sequence showed heterogeneity of the N-terminal portion of the molecule. Three forms were found, having the following N-terminal sequences:

Met-Ala-Pro-Ile-Thr-Ala-Tyr-Ser-Gln-Gln-Thr (form 1) (SEQ ID NO:48)

Pro-Ile-Thr-Ala-Tyr-Ser-Gln-Gln-Thr (form 2) (residues 3-11 SEQ ID NO:48)

Ser-Gln-Gln-Thr (form 3) (residues 8-11 SEQ ID NO:48)

To avoid this problem, two experimental strategies were adopted:

1. Homogenisation in the presence of 100 µg/ml of the chymostatin protease inhibitor. This inhibitor does not inhibit HCV protease activity, but it does inhibit the chymotrypsin type proteases, specific for aromatic residues like phenylalanine and tyrosine. In this way it was possible to purify a single molecular species with more than 95% of form 2.

2. Production of a protease corresponding to form 3 by means of the plasmid pT7-7 (NS3 1033–1206). In this way a protein with more than 95% of form 3 was purified.

EXAMPLE 3

Method for Reproducing in vitro the Activity of the HCV NS3 Protease

Definition of the Chemical and Physical Conditions for Reproduction of the Activity The ability of the purified protease to catalyse cleavage of the peptide Fmoc-Tyr-Gln-Glu-Phe-Asp-Glu-Met-Glu-Glu-Cys-Ala-Ser-His-Leu-Pro-Tyr-Ile-Glu-Gln-Gly (SEQ ID NO:7) has been used to define the optimum conditions for activity. Cleavage was detected by separating the substrate from the hydrolysis products by reverse-phase HPLC. For this purpose the mixture containing the buffer and the peptide incubated with the protease was injected into a reverse-phase Lichrospher RP-18 column (Merck) and eluted with an acetonitrile gradient containing 0.10% trifluoracetic acid. The cleavage products were identified by co-injection of appropriate standards, and by mass spectrometry. For these experiments, proteins produced by one of the methods described in examples 1 and 2 were used.

Figure 3:
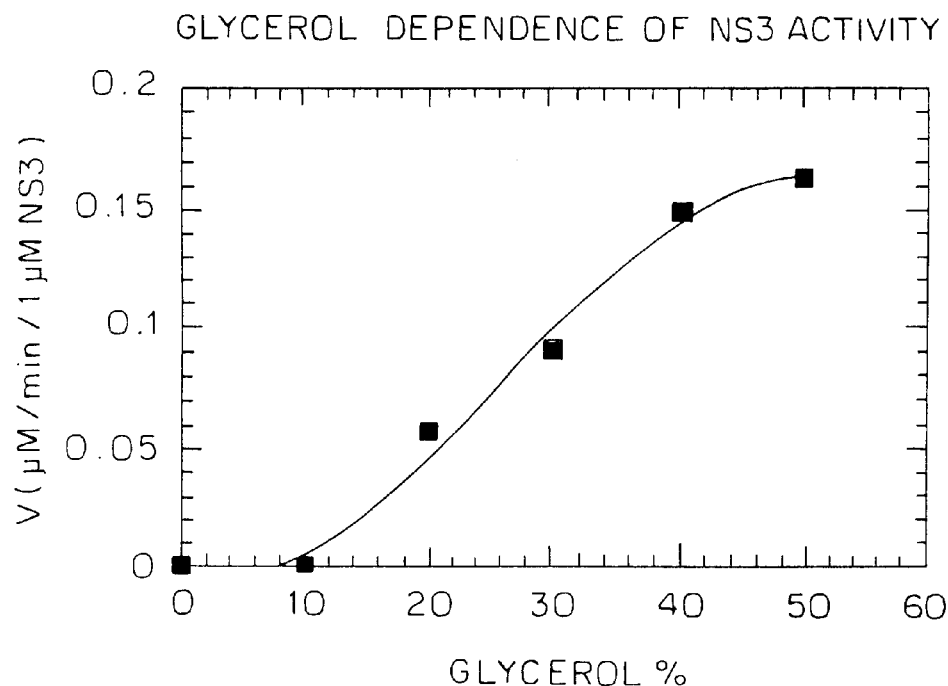
FIG. 3 shows NS3 activity as a function of the concentration of glycerol.
Figure 4:
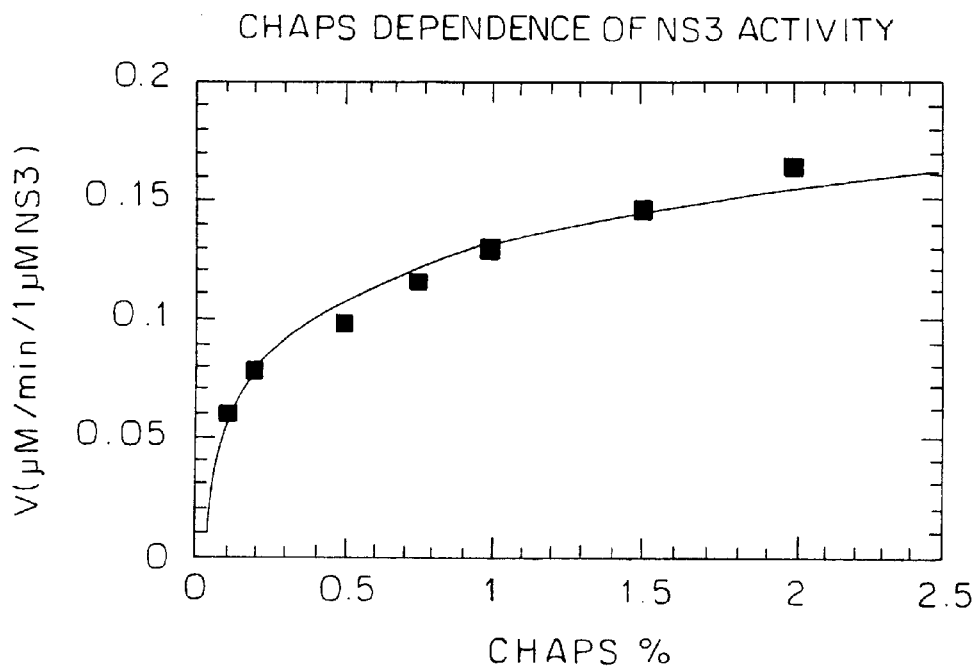
FIG. 4 shows NS3 activity as a function of the concentration of CHAPS, 3-[(3-colammide-propyl)-dimethyl-ammonium]-1-propansulphonate.

Dependence of the activity on the glycerol concentration was determined in a buffer containing 50 mM Tris pH 7.5, 2% CHAPS, 30 mM DTT. Increasing concentrations of glycerol were added to this buffer, and the relative protease activity was determined. FIG. 3 shows the results of this experiment, indicating that 50% (v/v) glycerol is the optimum level. In a subsequent experiment this concentration was kept constant at 50% and the concentration of CHAPS was varied (FIG. 4). A level of 2% CHAPS (w/v) was in this way found to be the optimum concentration. It was possible to replace CHAPS with other detergents compatible with the need to maintain catalytic activity in the polypeptides according to the invention. Some of these detergents are: heptyl-β-D-glucopyranoside, decyl-β-D-glucopyranoside, decyl-β-D-glucomaltoside, nonyl-β-D-glucopyranoside, N-hexyl-β-D-glucopyranoside, octyl-β-D-glucopyranoside, octyl-β-D-thio-glucopyranoside, Nonidet P-40, TweeN-20.

Figure 5:
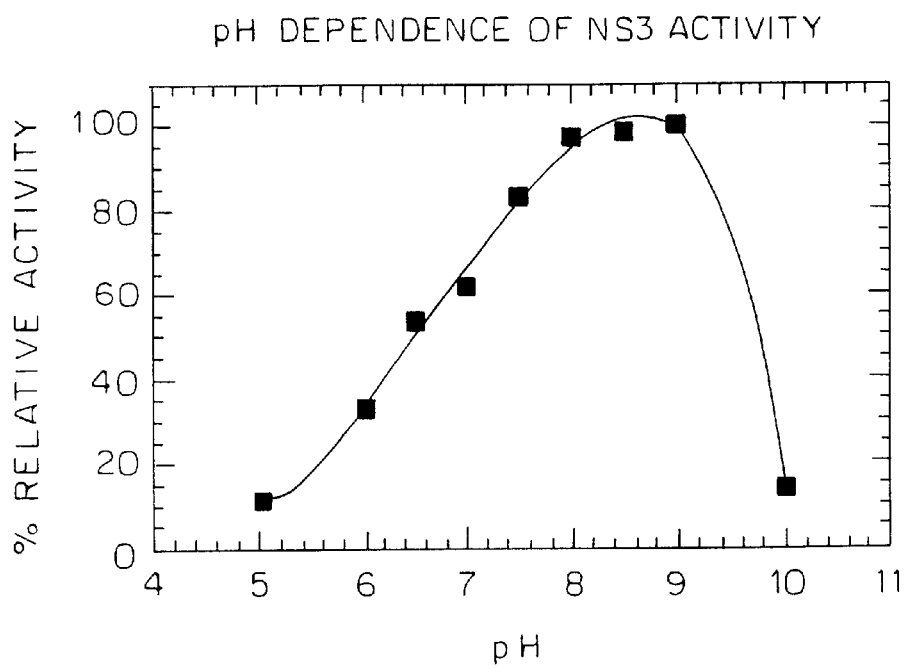
FIG. 5 shows NS3 activity as a function of pH.
Figure 6:
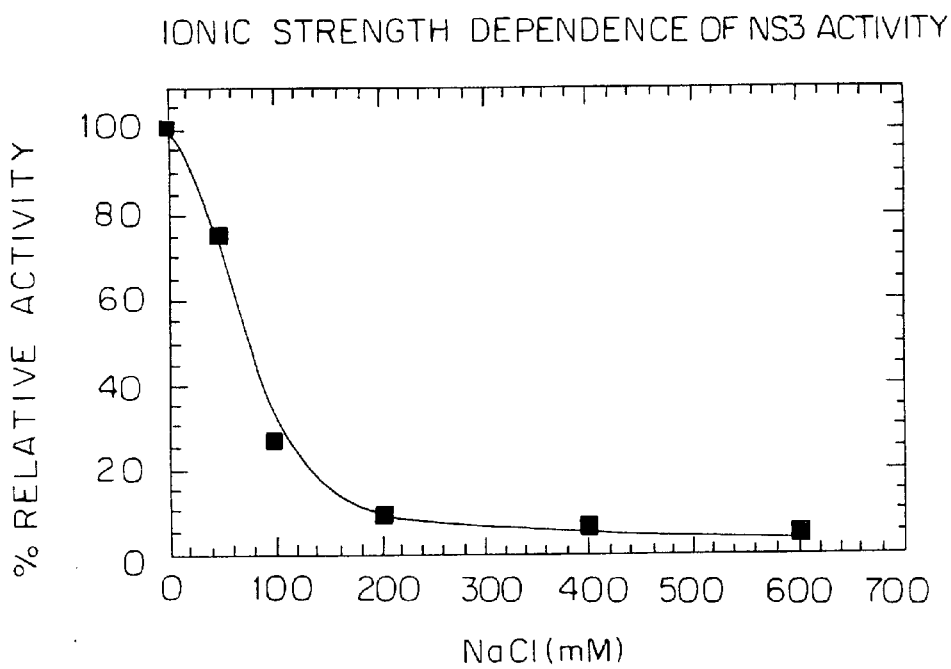
FIG. 6 shows NS3 activity as a function of ionic strength.
Figure 9:
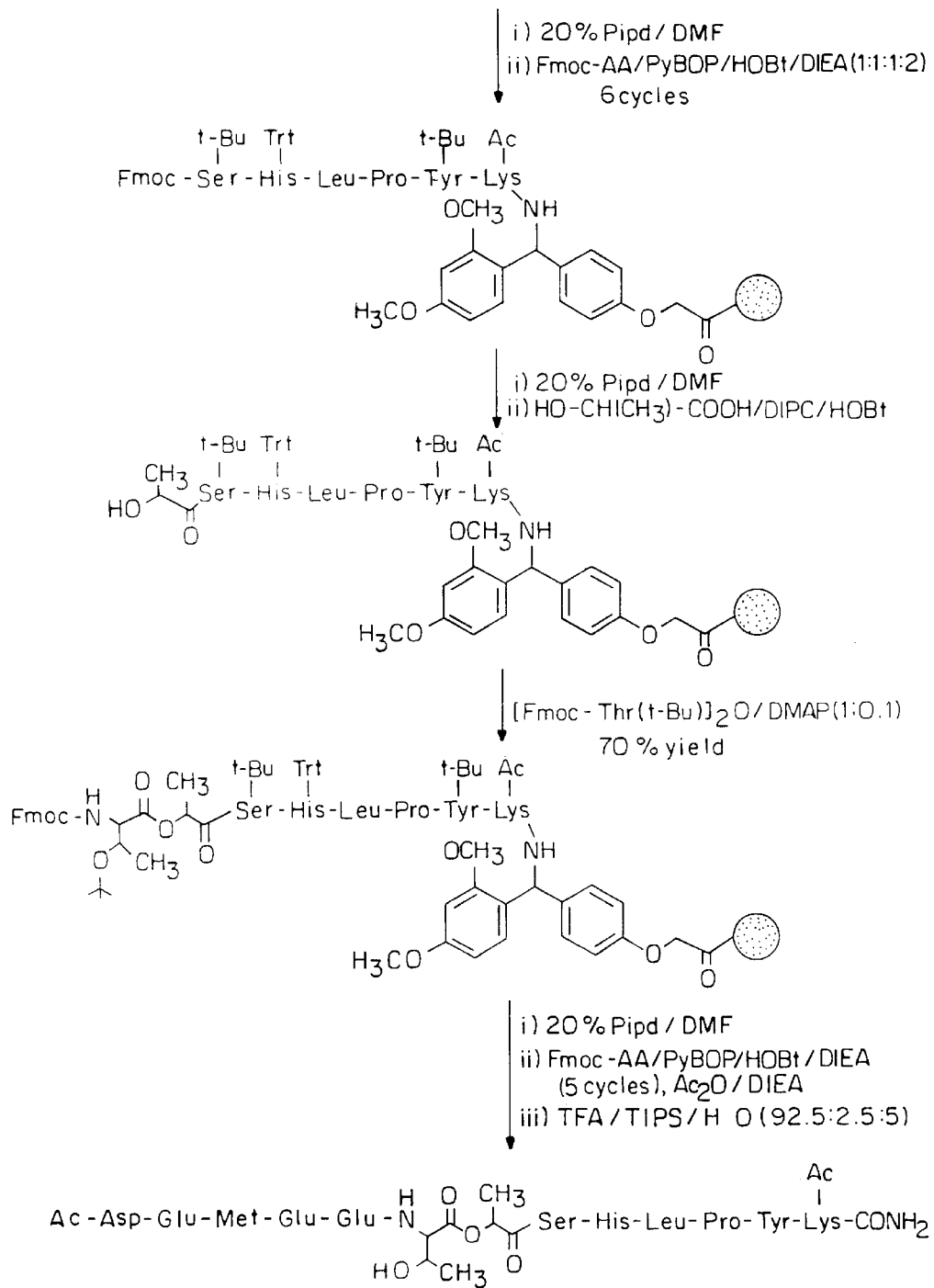
FIG. 9 shows the reaction diagram for synthesis of the depsipeptide substrate S2 represented by the sequence SEQ ID NO:43.

At optimum CHAPS and glycerol concentrations the protease shows optimal activity at pH 8.5 (FIG. 5). At this pH the stability over time is, however, lower than that seen at pH 7.5. To determine the effect of ionic strength on the activity, a titration was performed using NaCl. This experiment showed that protease activity is inhibited at a high ionic strength (FIG. 9). Kinetic analysis of data showed that chloride ions are competitive inhibitors at concentrations of up to 100 mM.

It was thus possible to define the following optimal conditions for in vitro assay of purified HCV protease activity: 50 mM Tris pH 7.5, 3–30 mM DTT, 2% CHAPS, 50% glycerol. Dependence of the activity on temperature was analysed by means of an Arrhenius plot in which the logarithm of the kinetic constant $K_{cat}$ is given as an inverse function of temperature. This graph shows discontinuity at temperatures above 25° C., indicating changes in conformation simultaneously to the decrease in activity. The optimum temperature was thus determined to be around 22–23° C.

As mentioned above, the protein NS4A is a cofactor of HCV protease. N and C-terminal deletion experiments have defined the peptide Pep4A with the sequence indicated in SEQ ID NO:6, as the minimum domain still capable of inducing optimal activation. In transfection or in vitro translation experiments the addition of polypeptides containing the minimum NS4A sequence is essential to give effective cleavage. The addition of Pep4A is capable of inducing a significant increase in the activity of purified protease in the assay conditions described above. The kinetic characteristics of this activation are described below. Using a titration experiment a stoichiometry of 1:1 was determined for this interaction at a concentration of 300 nm of protease, indicating a Kd<300 nM.

Definition of the Optimal Substrate for Activity Assay

To define the minimum substrate whose cleavage can still be detected using the HPLC method described above, derivatives of the peptide Fmoc-Tyr-Gln-Glu-Phe-Asp-Glu-Met-Glu-Glu-Cys-Ala-Ser-His-Leu-Pro-Tyr-Ile-Glu-Gln-Gly (SEQ ID NO:7) described above were synthetized, with N- and/or C-terminal deletions. These peptides were incubated in the conditions defined in the preceding chapter in the presence of 100 nM–1.6 μM protease. The nomenclature for the amino acid residues of the peptides used as substrates that is adopted in the following is that set down by Schechter and Berger in (7). The residues are defined as Pn . . . P3, P2, P1, P1', P2', P3' . . . Pn', where the hydrolysed bond is P1–P1' (bond between Cys and Ala). Table 1 shows the kinetic data for this experiment, defining P6 and P3' or P4' as the extreme limits of a substrate that is still effectively cleaved. Deletions beyond P6 or P3' cause a drastic decrease in effectiveness, measured as $k_{cat}/K_m$, with which the respective peptide can still act as a substrate. Deletion of P4' causes a less marked decrease of $k_{cat}/K_m$, however the separation of substrate and cleavage product by HPLC is significantly better for a decapeptide P6-P4' than for a nonapeptide P6-P3', so that the decapeptide P6-P4' has been defined the optimal substrate.

TABLE 1

Characterisation of substrate

| Peptide | | $K_m$ (μm) | $k_{cat}$ (min$^{-1}$) | $k_{cat}/K_m$ (HU$^{-1}$s$^{-1}$) |
|---|---|---|---|---|
| (SEQ ID NO: 7) | Fmoc-YQEFDEMEECASHLPYIEQG | 53 | 0.5 | 143.0 |
| (SEQ ID NO: 8) | Ac-YQEFDEMEECASHLPY | 56 | 0.3 | 87.0 |
| (SEQ ID NO: 9) | Ac-YQEFDEMEECASHLP | 95 | 0.4 | 70.2 |
| (SEQ ID NO:10) | Ac-YQEFDEMEECASHL | 117 | 0.4 | 51.0 |
| (SEQ ID NO:11) | Ac-YQEFDEMEECASH | 197 | 0.3 | 24.0 |
| (SEQ ID NO:12) | Ac-YQEFDEMEECAS | >1500 | — | 11.1 |
| (SEQ ID NO:13) | Ac-YQEFDEMEECA | | no cleavage | |
| (SEQ ID NO:14) | Ac-DEMEECASHLPY | 171 | 0.3 | 34.0 |
| (SEQ ID NO:15) | Ac-EMEECASHLP | 3137 | 0.3 | 2.0 |
| (SEQ ID NO:16) | Ac-MEECASHL | | no cleavage | |
| (SEQ ID NO:17) | Ac-ECASHLPYIEQG | | no cleavage | |

TABLE 1-continued

Characterisation of substrate

| Peptide | $K_m$ ($\mu$m) | $k_{cat}$ (min$^{-1}$) | $k_{cat}/K_m$ (HU$^{-1}$s$^{-1}$) |
|---|---|---|---|
| (SEQ ID NO:18) Ac-DEMEECASHL | 100 | 0.3 | 47 |
| (SEQ ID NO:19) DEMEECASHL | 85 | 0.1 | 22.7 |
| (SEQ ID NO:20) Fmoc-DEMEECASHL | 95 | 0.1 | 23.8 |

The kinetic parameters $K_m$, $k_{cat}$ and $k_{cat}/K_m$ were determined for decapeptides P6-P4' corresponding to the other two intermolecular cleavage sites NS4B/5A and NS5A/5B and this data was compared with the data obtained using the peptide P6-P4' corresponding to the site NS4A/4B (table 2). These kinetics were obtained both in the absence and in the presence of stechiometric concentrations of Pep4A. Analysis of the kinetic data obtained in this fashion indicates that Pep4A prevalently affects $k_{cat}$. When the $K_m$ values for the single substrates are compared it becomes evident that the presence of two negative charges in P5 and in P6 determined the bonding effectiveness of a peptide substrate. In fact decapeptides corresponding to the sites NS4A/4B and NS5A/5B with Asp or Glu residues in position P6 and P5 have $K_m$ values similar and significantly lower than the peptide corresponding to site NS4B/5A with a single charge in position P6.

TABLE 2

Activity on peptides corresponding to cleavage sites in trans

| Peptide | $K_m$ ($\mu$M) | $k_{cat}$ (min$^{-1}$) | $k_{cat}/K_m$ (M$^{-1}$s$^{-1}$) |
|---|---|---|---|
| NS4A/4B | | | |
| (SEQ ID NO:18) Ac-DEMEECASHL | 100 | 0.3 | 47.0 |
| (SEQ ID NO: 6) + pep4A | 43 | 1.4 | 540 |
| NS4B/5A | | | |
| (SEQ ID NO:21) Ac-DCSTPCSGSW | 2100 | 0.05 | 0.4 |
| (SEQ ID NO: 6) +pep4A | 320 | 0.8 | 4.2 |
| NS5A/NS5B | | | |
| (SEQ ID NO:22) AC-EDVVCCSMSY | 310 | 4.2 | 220 |
| (SEQ ID NO: 6) +pep4A | 380 | 15 | 650 |

Further investigation was carried out on the relative importance of single residues within the sequence P6-P4', corresponding to the cleavage site NS4A/4B, by mutating each amino acid singly to alanine and then determining the kinetic parameters for the mutant peptides obtained in this way. The results are described in table 3. This experiment identifies the following scale of importance of single residues for effective cleavage: P1>>P3=P5=P6>P2=P4. Modification of the P' part does not have a significant effect on the rate of cleavage. This information was used to develop protease activity assay methods, useful for the identification of inhibitors. These methods will be described below.

TABLE 3

Replacement with alanine of residues P6-P4' of the peptide substrate

| Peptide | $K_m$ ($\mu$M) | $k_{cat}$ (min$^{-1}$) | $k_{cat}/K_m$ (M$^{-1}$s$^{-1}$) |
|---|---|---|---|
| (SEQ ID NO:18) Ac-DEMEECASHL | 100 | 0.3 | 47.0 |
| (SEQ ID NO:23) Ac-AEMEECASHL | 150 | 0.1 | 9.4 |
| (SEQ ID NO:24) Ac-DAMEECASHL | 527 | 0.3 | 9.3 |
| (SEQ ID NO:25) Ac-DEAEECASHL | 114 | 0.1 | 18.1 |
| (SEQ ID NO:26) Ac-DEMAECASHL | 322 | 0.1 | 7.2 |
| (SEQ ID NO:27) Ac-DEMEACASHL | 132 | 0.1 | 18.4 |
| (SEQ ID NO:28) Ac-DEMEEAASHL | | no cleavage | |
| (SEQ ID NO:29) Ac-DEMEECAAHL | 129 | 0.2 | 32.5 |
| (SEQ ID NO:30) Ac-DEMEECASAL | 180 | 0.3 | 33.4 |
| (SEQ ID NO:31) Ac-DEMEECASHA | 94 | 0.1 | 23.2 |

For more detailed determination of the importance of the residues in P6 and P1', a series of peptides P6-P4' were synthetised in which modifications were introduced in these positions. The results of these experiments are described in table 4. The results of these experiments underline the importance of a negative charge in position P6. In fact, Asp or Glu in this position are accepted with indistinguishable $K_m$. Neutralisation of the charge by introduction of Asn causes a significant increase in $K_m$, whereas inversion of the charge by introduction of a Lys residue causes an extremely marked increase in $K_m$.

TABLE 4

Substitution of residues P6 and P1' in the peptide substrate

| Peptide | $K_m$ ($\mu$M) | $k_{cat}$ (min$^{-1}$) | $k_{cat}/K_m$ (M$^{-1}$s$^{-1}$) |
|---|---|---|---|
| (SEQ ID NO:18) Ac-DEMEECASHL | 100 | 0.3 | 47.0 |
| (SEQ ID NO:32) Ac-EEMEECASHL | 85 | 0.2 | 32.0 |
| (SEQ ID NO:33) Ac-NEMEECASHL | 427 | 0.2 | 7.7 |

TABLE 4-continued

Substitution of residues P6 and P1' in the peptide substrate

| Peptide | $K_m$ ($\mu$M) | $k_{cat}$ (min$^{-1}$) | $k_{cat}/K_m$ (M$^{-1}$s$^{-1}$) |
|---|---|---|---|
| (SEQ ID NO:34) Ac-KEMEECASHL | >1000 | — | 3.1 |
| (SEQ ID NO:35) Ac-DEMEECSSHL | | | 27.2 |
| (SEQ ID NO:36) Ac-DEMEECFSHL | | | 1.1 |

Substitution of Ala in position P1' with Ser has no significant effect, whereas substitution with Phe causes a reduction in the cleavage rate of the resulting substrate, measured as $k_{cat}/K_m$.

Analysis was carried out on a series of mutations of the position P1, described in table 5. Substitution of cysteine in this position with threonine, alylglycine, α-aminobutyric acid, norvaline and valine are accepted, even though the resulting substrates are cleaved with an efficiency, expressed as $k_{cat}/K_m$, which is significantly lower than that of the unmodified substrate.

TABLE 5

Substitution of the peptide substrate residue P1

| Peptide substrate | $k_{cat}/K_m$ (M$^{-1}$s$^{-1}$) |
|---|---|
| (SEQ ID NO:18) Ac-DEMEECASHL | 47.0 |
| (SEQ ID NO:37) Ac-DEMEEAlgASHL | 4.3 |
| (SEQ ID NO:38) Ac-DEMEEAbuASHL | 1.2 |
| (SEQ ID NO:39) Ac-DEMEETASHL | 0.6 |
| (SEQ ID NO:40) Ac-DEMEENvaASHL | 0.08 |
| (SEQ ID NO:41) Ac-DEMEEVASHL | 0.05 |

Alg, alylglycine; Abu, α-aminobutyrric acid; Nva, norvaline

The information relating to substrate specificity can be used both for development of enzyme assays and for synthesis of inhibitors based on modified substrate sequences. For example, substrate peptides with modified P1 residues are competitive inhibitors of protease with inhibition constants Ki of between 350 and 90 $\mu$M (table 6). These peptides can be further modified to increase their inhibitory power by introduction of aldehyde, trifluoromethylketone, difluoromethylenketone, diketone, ketoester, ketoamide or α-ketoheterocyclic, boronic acid and monoalomethylketone groups. Information on specificity can also allow synthesis of inhibitors that are not based on peptides, such as: haloenolactones, isocoumarines, β-lactames, succinimides, pyrones, bezoxyazynones, bezoiso-thiazolines or latent isocyanates.

TABLE 6

Inhibitory action of decapeptides P6-P4' modified at position P1

| residue P1 | Ki ($\mu$M) | $K_m$ ($\mu$M) |
|---|---|---|
| Cys | — | 90 |
| Abu | 175 | 189 |
| Alg | 165 | 179 |
| Thr | 215 | 180 |
| Val | 173 | not determined |
| Ala | 173 | no cleavage |
| Ser | 90 | no cleavage |
| Gly | 191 | no cleavage |
| Pro | 440 | no cleavage |
| Cha | 350 | no cleavage |

Abu, α-aminobutyric acid; Alg, alylglycine; Cha, ciclohexylalanin.

EXAMPLE 4

Method for Using in vitro Protease Activity for Inhibitor Research

Automatic Assay Using an Amide Substrate

Figure 7:
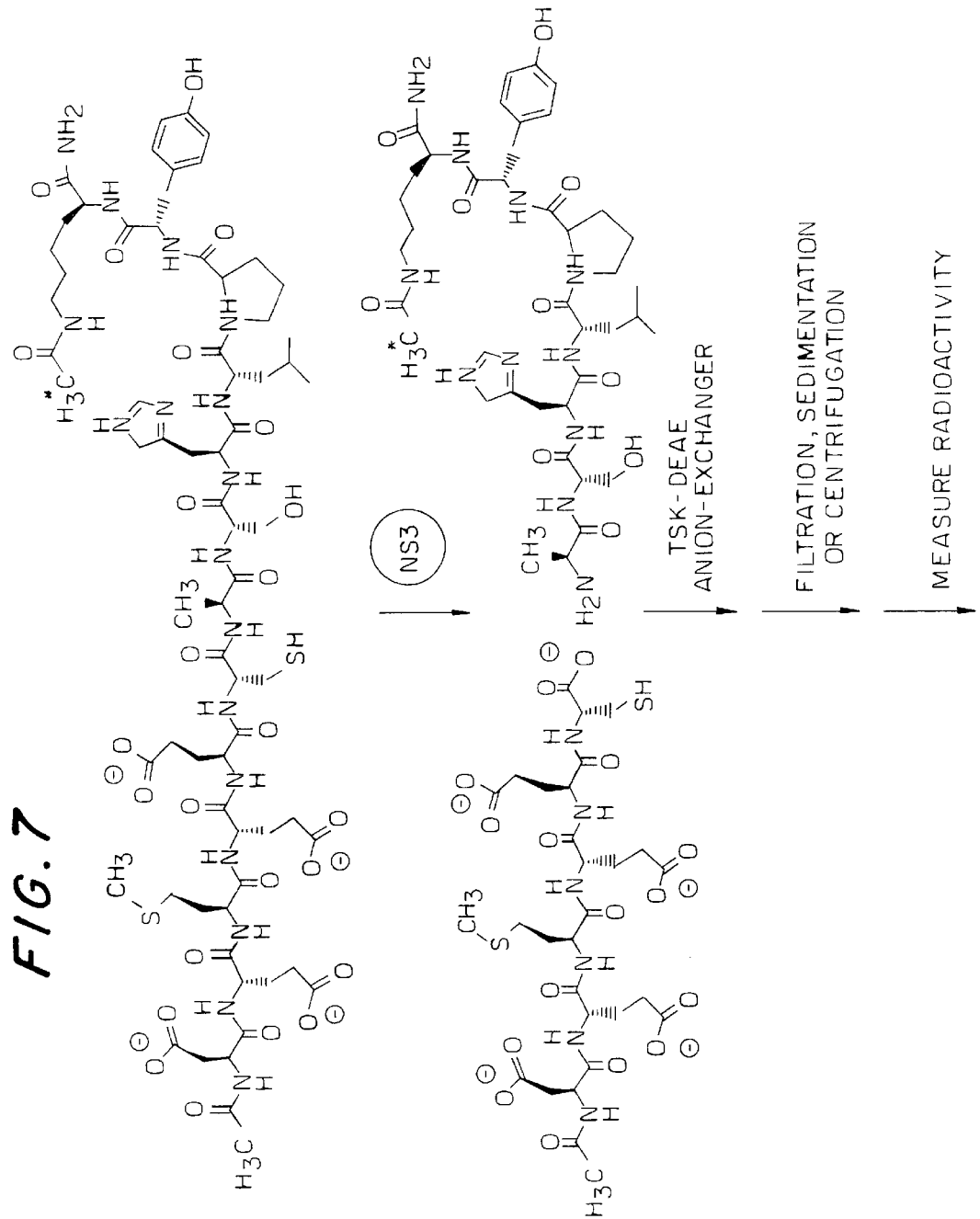
FIG. 7 shows a diagram of the enzymatic assay to measure NS3 activity using as a substrate a peptide Ac-Asp-Glu-Met-Glu-Glu-Cys-Ala-Ser-His-Leu-Pro-Tyr-Lys-ε-($3^H$)-Ac (SEQ ID NO:47).

The peptide Ac-Asp-Glu-Met-Glu-Glu-Cys-Ala-Ser-His-Leu-Pro-Tyr-Lys-ε-($^3$H)Ac, (SEQ ID NO:47) derived from the cleavage site NS4A/NS4B, is cleaved by the NS3 protease with the following kinetic parameters: $K_m$=79 $\mu$M, $k_{cat}$=0.49 min$^{-1}$ and $k_{cat}/K_m$=103 M$^{-1}$ s$^{-1}$. 400,000 cpm of the labelled peptide with a specific activity of 2–10 Ci/mmol. were incubated for 3 hours at 23° C. together with 40 $\mu$M ($K_m$/2) of unlabeled peptide in the presence of 200 nM protease and 1 $\mu$M of Pep4A in 50 mM Tris pH 7.5, 50% glycerol, 3% CHAPS, 10 mM DTT. During this period 20% of the peptide substrate was cleaved. The cleavage product can be quantified following the method described below and summarised in FIG. 7. As can be seen from the figure, the mixture is placed in contact with a TSK-DEAE anionic exchanger. The fraction coming out of the exchanger is filtered, allowed to sediment or spun. The radioactivity is measured on the clear fraction, the amount of which is exclusively related to the right fragment (C-terminal), given that the amide substrate and the left hand fragment remain bound to the anionic exchanger. The addition of inhibitors causes a decrease in the release rate of the labelled cleaved fragment. The more effective the inhibitor, the lower will be the radioactivity measured in the fraction coming out of the anionic exchanger.

EXAMPLE 5

Synthesis of the Depsipeptide Substrate S1: Ac-Asp-Glu-Met-Glu-Glu-Abu-ψ[COO]-Ala-Ser-His-Leu-Pro-Tyr-Lysa (N$^ε$-Ac-NH$_2$ (SEQ ID NO:8)

Figure 8:
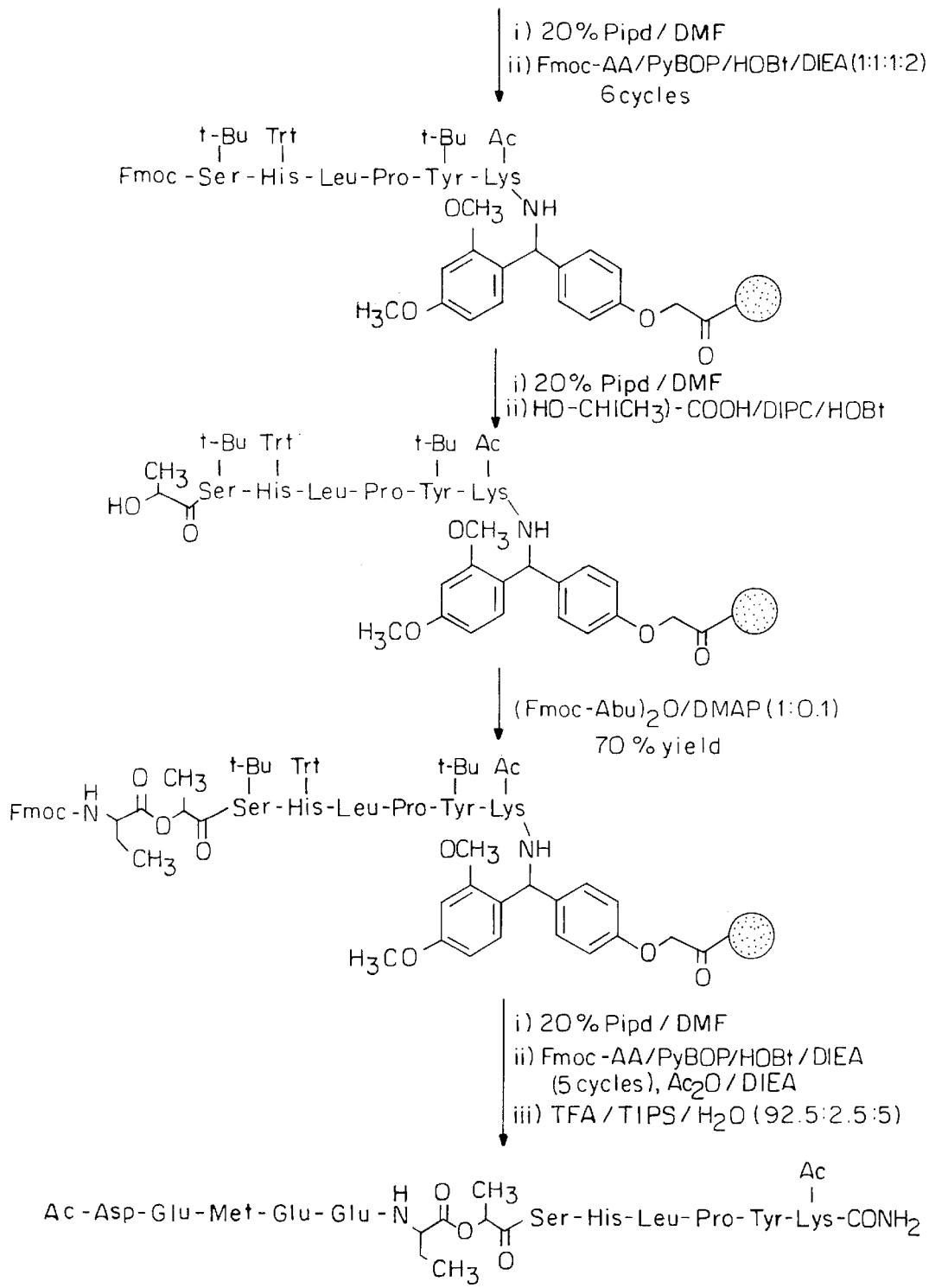
FIG. 8 shows the reaction diagram for synthesis of the depsipeptide substrate Si represented by the sequence SEQ ID NO:42.

The synthesis was performed entirely on solid-phase using the continuous-flow Fmoc-polyamide method (9). The protecting group combination was: base-labile Nα-Fmoc for the α-amino group and acid-labile protection for the side-chains: Asp(Ot-Bu), Glu(Ot-Bu), Tyr(t-Bu) and His(trt). The polymer used was composite Kieselguhr-polyamide (9) derivatised with a modified Rink amide linker (10), p-[(R,S)-a-[1-(9H-Fluoren-9 -yl)-methoxyformamido]-2,4-dimethoxybenzyl]-phenoxyacetic acid (11) (NovaSyn® KR 125, 0.1 mmol/g). The resin, amino acid derivatives, activating agents and all other reagents were of the highest available grade from commercial sources. The synthesis was run according to the scheme given in FIG. 8. Couplings were performed with 5-fold excess of activated amino acid over the resin free amino groups, using Fmoc-amino acid/PyBOP/HOBt/DIEA (1:1:1:2) activation, except for L-(+)- lactic acid where Fmoc-amino acid/DIPC/HOBt (1:1:1:1) activation was used. Esterification of Abu to the free hydroxyl of lactic acid was performed using the symmetrical anhydride (Fmoc-Abu)2O in the presence of a catalytic amount (0.1 equiv.) or DMAP, for 30 minutes at room temperature (12): the reaction was repeated twice to achieve 90% yield; in the absence of catalyst, the remaining free hydroxyls are unreactive in subsequent synthetic operations. At the end of the assembly, the resin was washed with DMF, methanol and $CH_2Cl_2$, then dried in vacuo for 16 hours. The dry peptide-resin was treated with TFA/water/ triisopropylsilane (92.5:5:2.5) for 1.5 hours at room temperature; the resin was filtered out and the peptide precipitated with cold methyl t-Bu ether; the precipitate was redissolved in 50% water/acetonitrile containing 0.1% TFA and lyophilised.

Purification to >98% homogeneity was achieved through preparative HPLC on a Nucleosyl C-18 column (250×21 mm, 7 μM) using as eluents (A) water and (B) acetonitrile with 0.1% TFA, and a step gradient 22%B over 5 minutes, then 22–27%B over 25 minutes, flow rate 12 ml/min. In these conditions the peptide elutes at 21.9 minutes. The fractions containing the pure material were pooled and lyophilised: yield 35%.

EXAMPLE 6
Chemical Synthesis of the Desi-Pentide Substrate S2: Ac-Asp-Glu-Met-Glu-Glu-Thr-ψ-[CCOO]1-Ala-Ser-His-Leu-Pro-Tyr-Lys($N^\epsilon$-Ac)-$NH_2$ (SEQ ID NO:43)

The synthesis was performed as described in the previous example. Esterification of Thr to lactic acid required three repetitions to obtain a 70% yield, which was also accompanied by 3% racemization of the Thr residue. The D-Thr diastereoisomer was however chromatographically well resolved from the L-isomer, and easily resolved by preparative HPLC. The gradient used was 21%B over 5 minutes, then 21–22%B over 20 minutes, with the desired peptide eluting at 19.7 minutes: yield 24%.

EXAMPLE 7
Synthesis of the Radioactive Densipeptide Substrate S1: Ac-Asp-Glu-Met-Glu-Glu-Abu-ψ-[COO]-Ala-Ser-His-Leu-Pro-Tyr-Lys($N^\epsilon$-[$^3$H]-$CH_3$CO)-$NH_2$ (SEQ ID NO:44)

Figure 10:
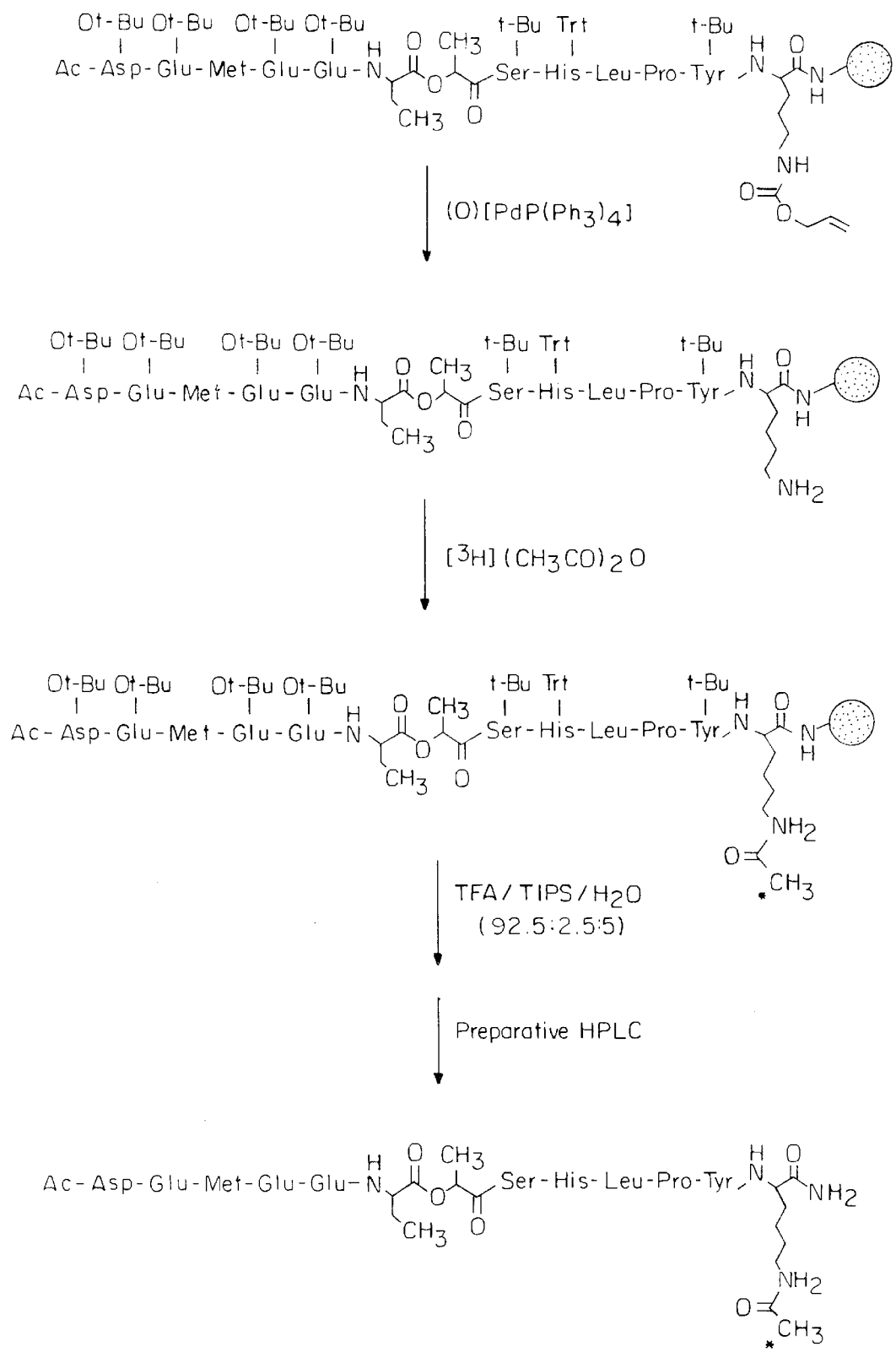
FIG. 10 shows the reaction diagram for synthesis of the radioactive depsipeptide substrate S1 represented by the sequence SEQ ID NO:44.

To selectively label peptide S1 on the $N^\epsilon$-amino group of the C-terminal lysine, the protected precursor Ac-Asp(Ot-Bu)-Glu(Ot-Bu)-Met-Glu(Ot-Bu)-Glu(Ot-Bu)-Abu-ψ [COO]-Ala-Ser(t-Bu)-His(Trt)-Leu-Pro-Tyr(t-Bu)-Lys-$CONH_2$ was assembled on the resin according to the scheme of FIG. 10. The only variation with respect to the synthesis of ($N^\epsilon$-Ac)-S1 was the use of Fmoc-Lys(Alloc)-OH instead of Fmoc-Lys($N^\epsilon$-Ac)-OH. The Alloc protection is orthogonal with respect to Fmoc and t-Bu based protecting groups, being removed with a two hour treatment with (0) PdP[($Ph_3$)$_4$] in a solution of $CHCl_3$ containing 5% acetic acid and 2.5% N-methylmorpholine.

The dry peptide-resin (0.07 mmol/g, 60 mg) was reacted with [$^3$H] acetic anhydride (25 mCi, 5.7 mCi/mmol) for 16 hours at room temperature. A 10-fold excess of non-radioactive acetic anhydride was then used to complete the reaction. The resin was then washed with DMF and treated as previously described. After preparative HPLC, >98% pure peptide Ac-Asp-Glu-Met-Glu-Glu-Abu-•-[COO]-Ala-Ser-His-Leu-Pro-Tyr-Lys($N^\epsilon$-[$^3$H]-$CH_3$CO)-$NH_2$ (SEQ ID NO:44) was obtained with a specific activity of 0.68 mCi/mmol.

Using the HPLC-based assay, the following kinetic parameters were obtained for the radioactive depsipeptide substrate S1 (SEQ ID NO:44):

$K_{cat}$ (min$^{-1}$)=9
$K_m$ (μM)=11
$K_{cat}/K_m$($M^{-1}s^{-1}$)=13.636

Using the same assay, the kinetic parameters for the radioactive substrate S2 are
$K_{cat}$ (min$^{-1}$)=16
$K_m$(μM)=96
$K_{cat}/K_m$($M^{-1}s^{-1}$)=2.780.

Figure 11:
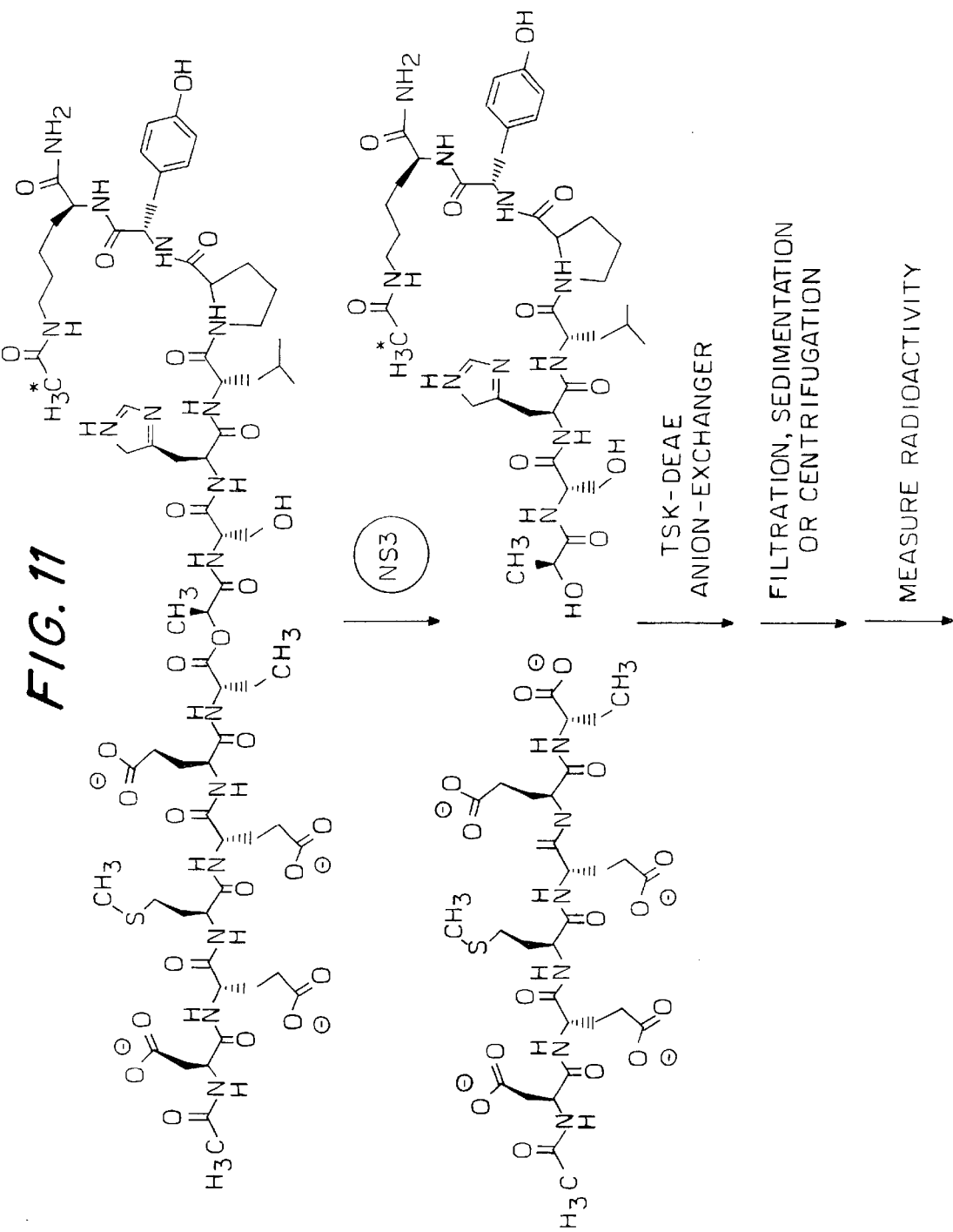
FIG. 11 shows a high-throughput assay, based on radioactive signals, to determine NS3 protease activity.

Synthesis of the radioactive depsipeptide substrates allows set-up of a high-throughput assay for determination of NS3 protease activity as schematically illustrated in FIG. 11. The principle is the following: both the intact substrate and the N-terminal fragment that originates from enzyme cleavage (Ac-Asp-Glu-Met-Glu-Glu-Abu-OH) (SEQ ID NO:49) are extremely acid, whereas the C-terminal fragment [HO-CH($CH_3$)CO-Ser-His-Leu-Pro-Tyr-Lys($N^\epsilon$-[$^3$H]-$CH_3$CO)-$NH_2$] (SEQ ID NO:50) is, according to pH, neutral or basic. It is therefore possible to capture the two acidic species on an anionic exchange resin, leaving the C-terminal fragment in solution. If the C-terminal fragment contains a radioactive marker (in this case the tritiated acetate covalently bonded to the ε-amino group of the C-terminal lysine), the resin will be able to discriminate processed substrate from non-processed substrate, thus making it possible to quantify proteolytic activity by measuring the amount of radioactivity remaining in solution after incubation with the enzyme and treatment with the ion exchanger. The whole process is essentially the same used in the high-throughput assay based on the amide substrate of example 4, but the pH used in this case is 7.0 instead of 7.5 to minimise spontaneous hydrolysis of the ester bond (0.6%/hour at 23° C.).

EXAMPLE 8
Synthesis of the Depsipeptide Substrates S3 and S4: Ac-Asp-Glu-Asp-(EDANS)-Glu-Glu-Abu-ψ[COO)-Ala-Ser-Lys-(DABCYL)$NH_2$ (SEQ ID NO:45) and Ac-Asp-Asp-(EDANS)-Met-Glu-Glu-Abu-ψ[COO}-Ala-Ser-Lys (DABCYL)$NH_2$ (SEQ ID NO:46)

The chemical formula of the two substrates S3 and S4 is shown in FIG. 11.

Figure 13:
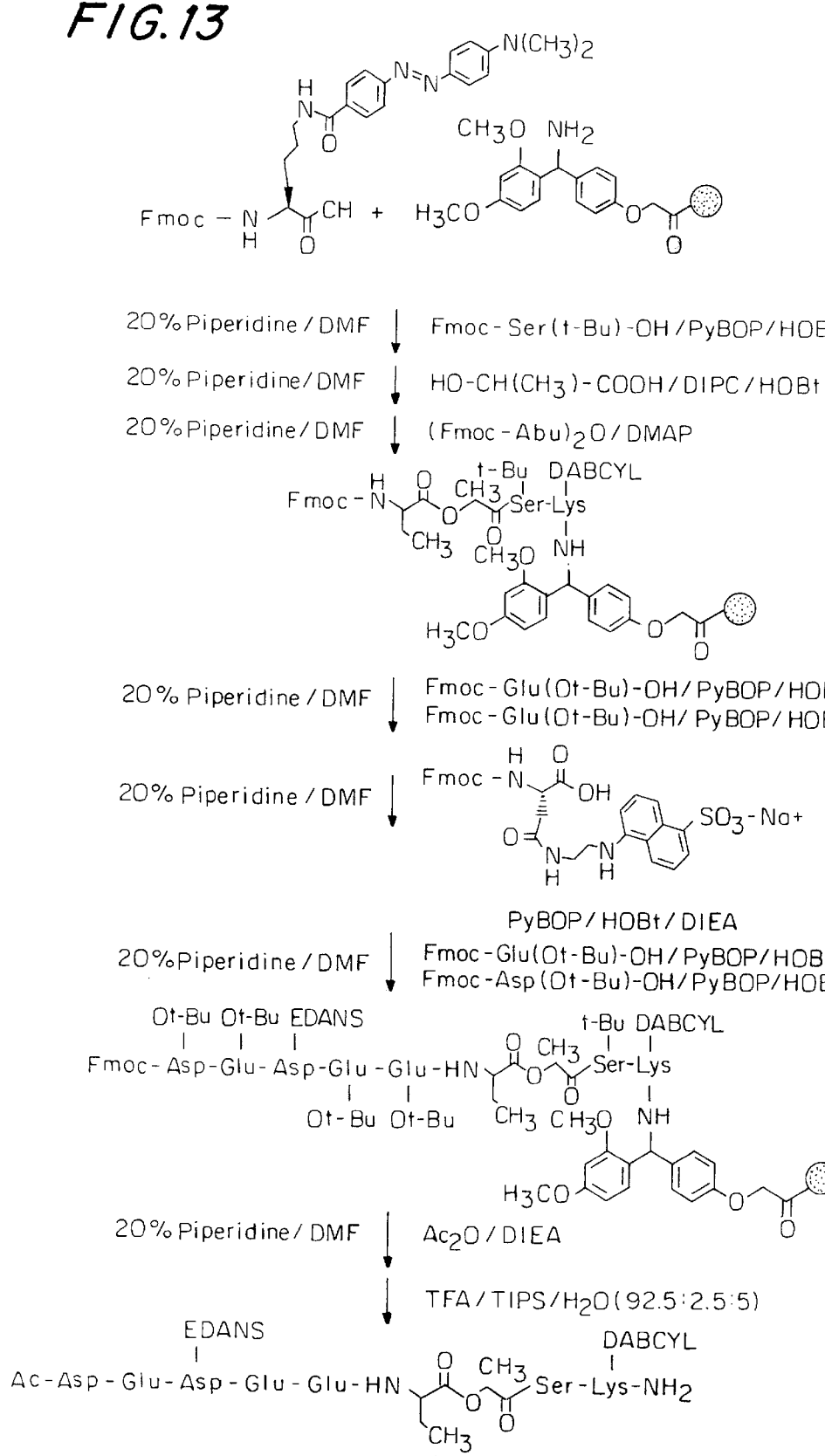
FIG. 13 shows the reaction diagram for synthesis of the depsipeptide substrate S3 (SEQ ID NO:45).

The synthesis was performed on solid phase as detailed in the scheme of FIG. 13 for S3 (SEQ. ID NO:45), making use of two special derivatives, Fmoc-Asp(EDANS)-OH and Fmoc-Lys(DABCYL)-OH, prepared according to known methods (16–17). All the couplings, including Asp(EDANS) and Lys(DABCYL), were performed with 5-fold excess of activated amino acid over the resin free amino groups, using Fmoc-amino acid/PyBOP/HOBt/DIEA (1:1:1:2) activation, with the exception of L-(+)-lactic acid where Fmoc-amino acid/DIPC/HOBt (1:1:1.1) activation was used. Esterification of Abu to the free hydroxyl of lactic acid was performed using the symmetrical anhydride (Fmoc-Abu)$_2$O in the presence of a catalytic amount (0–1 equiv.) of DMAP, for 30 minutes at room temperature (12): the reaction was repeated twice to achieve 92% yield. At the end of the assembly, the peptide-resin was washed and the peptide cleaved as described for substrate S1.

Figure 14A:
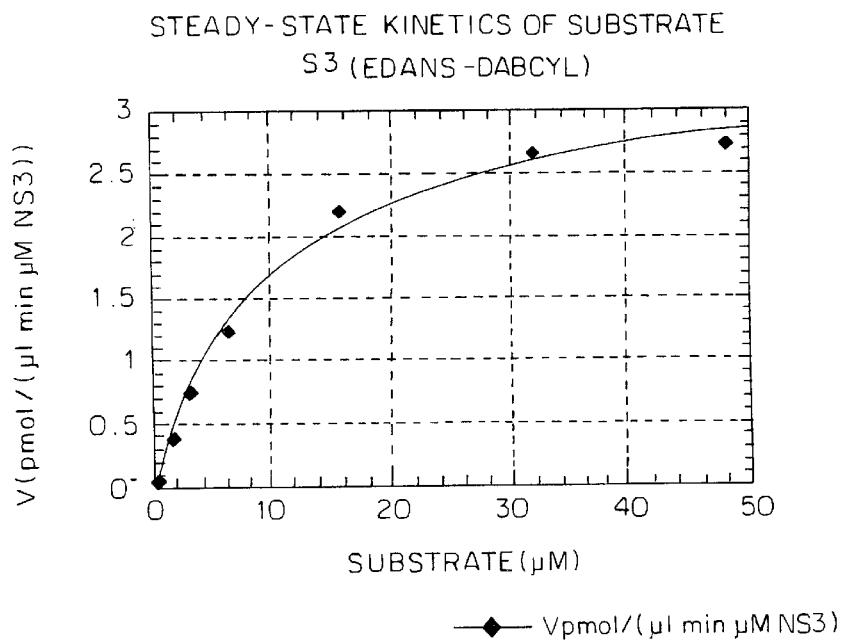
FIGS. 14A and 14B show, respectively, the kinetic parameters for the NS3 protease with the substrate S3 (SEQ ID NO:45) and fluorescence as a function of time in the relevant assay.

Purification to >98% homogeneity was achieved through preparative HPLC on a Nucleosyl C-18 column (250×21 mm, 7 μm) using as eluents (A) 50 mM ammonium acetate, pH 6 and (B) acetonitrile. The gradient used for both S3 and S4 was 20%B over 5 minutes, then 20–40%B over 20 minutes, flow rate 20 ml/min; the fractions containing the pure material were pooled and lyophilised: yield 45% and 35% for S3 and S4, respectively. The kinetic parameters for this substrate, evaluated through the HPLC-based assay (see FIG. 14A), were the following:

$K_{cat}$(min$^{-1}$)=3.51
$K_m$($\mu$M)=10.95
$K_{cat}/K_m$(M$^{-1}$s$^{-1}$)=5342.

Figure 14B:
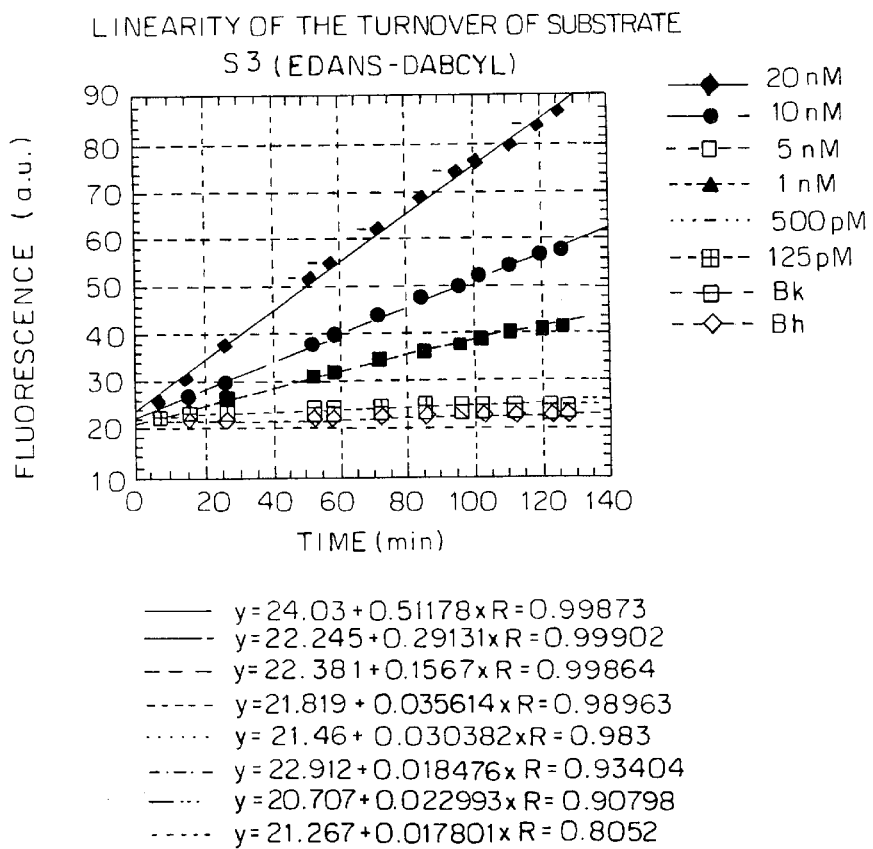

The buffer used for the assay is the following: 33 mM DTT, 50 mM Tris, pH 7, 50% glycerol, 2% CHAPS. The incubation is carried out at pH 7.0 to minimise spontaneous hydrolysis of the ester bond. The assay can be run in a cuvette or in a (96-well) microtitre plate, monitoring the fluorescence as a function of time (Excitation wavelength 355 nM, Emission wavelength 495 nM). The increase in fluorescence upon substrate cleavage is 13-fold. The reaction is linear as shown in FIG. 14B (fixed substrate concentration=2 $\mu$M). The detection limit was established as 1 nM for the high-throughput microplate assay and 520 pM for the HPLC-based assay. If a continuous (cuvette) assay is performed to establish initial rates for the enzymatic reaction, the lower limit for enzyme concentration is 80 nM, because of fluorescence quenching of the cleaved substrate at substrate concentrations higher than 10 $\mu$M.

Deposits

Strains of *E. coli* DH1—transformed using the plasmids pBac (1039–1226), pT7-7 (1039–1226), pT7-7 (1039–1206), pT7-7 (1027–1206) and pT7-7 (1033–1206) coding, respectively, for the polypeptides with amino acid sequence SEQ ID NO:1, SEQ ID NO:2, SEQ ID NO:3, SEQ ID NO:4 and SEQ ID NO:5—were deposited on Aug. 14, 1995 with The National Collections of Industrial and Marine Bacteria Ltd. (NCIMB), Aberdeen, Scotland, U.K., with access numbers NCIMB 40761, NCIMB 40762, NCIMB 40763, NCIMB 40764 and NCIMB 40765.

References

1. Chambers, T. J: et al 1990, Evidence that the N-terminal domain of non structural protein NS3 from yellow fever virus is serine protease responsible for site specific cleavages in the viral polyprotein, Proc. Natl. Acad. Sci. U.S.A. 87, 8898–8902.
2. Lam, P. Y. S. et al, 1994, Rational design of potent, bioavailable, nonpeptide cyclic ureas as HIV protease inhibitors, Science 263, 380–384.
3. Luckow, V. A., Baculovirus systems for the expression of human gene products, (1993) Current Opinion in Biotechnology 4, 564–572.
4. O'Reilly, D. R., Miller, L. K., Luckow, V. A., (1992), Baculovirus Expression Vectors—A Laboratory Manual, W. H. Freeman and Company, New York.
5. Studier and Moffatt, Use of Bacteriophage T7 RNA polymerase to-direct selective high level expression of cloned genes, (1986), J. Mol. Biol. 189, 113–130.
6. Thatcher and Hitchcock, Protein folding in Biotechnology, in: Mechanism of protein folding (edited by R. H. Pain), 226–263, IRL Press Oxford, New York, Tokyo, (1994).
7. Schechter and Berger, 1968, On the size of the active site in proteases I papain, Biochem. Biophys, Res. Communs. 27, 127–162.
8. Fersht, A. (1985) Enzyme structure and mechanism, W. H. Freeman, New York.
9. Atherton, E., Brown, E., Sheppard, R. C. and Rosevear, A. (1981) J. Chem. Soc., Chem. Commun., 1151.
10. Rink, H.. (1987) Tetrahedron Lett. 28, 3782.
11. Bernatowicz, M. S., Daniels, S. B. and Koster, H. (1989) Tetrahedron Lett. 30, 4645.
12. Atherton, E. and Sheppard, R. C. (1989) Solid phase peptide synthesis, a practical approach, IRL Press, Oxford.
13. Matayoshi, E. D., Wang, G. T., Krafft, G. A., and Erickson, J., (1990) Science 247, 954.
14. Maggiora, L. L., Smith, C. W. and Zhang, Z. Y. (1992) J. Med. Chem. 35, 3727.
15. Wang, G. T., Chung, G. C., Holzman, T. F. and Kraft, G. A. (1993) Anal. Biochem. 210, 351–359.
16. Andreae, F., Sommergruber, W., Gauss-Muller, V., Schultheis, T. and Ahorn, H. (1994) Innovations and Perspectives in solid Phase Synthesis, R. Epton, ed., Mayflower Worldwide Ltd., Birmingham, UK, pp. 433–436.
17. Kraft, G. A. and Wang. G. T. (1994) Methods Enzymol. 241, 70.
18. Pennington, M. W. and Thornberry, N. A. (1994) Peptide Res. 7, 72.
19. Holskin, B. P., Bukhtiyarova, M., Dunn, B. M., Baur, P., J. de Chastonay and Pennington, M. W. (1995) Anal. Biochem. 226, 148.

Abbreviation and Symobols Used in the Text

Abu=2-aminobutyric acid; CHAPS=3-[(3-colammide-propyl)-dimethyl-ammonium]-1-propansulphonate; DABCYL=4-[[4'-(dimethylaminophenyl]azo]benzoic acid; Depsipeptide=a peptide where at least one peptide bond is replaced by the corresponding ester bond (the location(s) of the ester bond(s) within the molecule is usually indicated as $\psi$[COO]— between the amino acid residues involved); DIEA=N,N-diisopropylethylamine; DIPC=N,N'-diisopropylcarbodiimide; DMAP=4-dimethylaminopyridine; DMF=N,N-dimethylformmamide; DTT=dithiothreitol; EDANS=5-[(2'-aminoethyl)amino]naphthalenesulfonic acid; EDTA=ethylendiamminotetracetic acid; HOBt=N-hydroxybenzotriazole; HPLC=high-performance liquid chromatography; PyBOP=Benzotriazole-1-yl-oxy-tris-pyrrolidino-phosphonium hexafluorophosphate; RET=resonance energy transfer; t-Bu=tertiary-butyl; TFA=trifluoroacetic acid; Trt(Trityl)=triphenylmethyl.

What is claimed is:

1. A depsipeptide consisting of between 8 and 12 amino acid residues and one α-hydroxy acid, which depsipetide has residues arranged in positions from P6 to P3' in the order P6-P5-P4-P3-P2-P1-P1'-P2'-P3', wherein:

the bond between residues P1 and P1' is an ester bond;

the residue in the P6 position is an amino acid residue selected from -he group consisting of Asp, Asn, and Glu;

the residue in the P5 position is an amino acid residue selected from the group consisting of Glu, Cys, and Asp;

the residue in the P4 position is an amino acid residue selected from the group consisting of Met, Ser, and Val;

the residue in the P3 position is an amino acid residue selected from the group consisting of Glu, Thr, and Val;

the residue in the P2 position is an amino acid residue selected from the group consisting of Met, Pro, and Cys;

the residue in the P1 position is 2-aminobutyric acid;

the residue in the P1' position is an α-hydroxy acid residue selected from the group consisting of an α-hydroxy acid corresponding in structure to Ala and Ser;

the residue in the P2' position is an amino acid residue selected from the group consisting of Ser, Gly, Met, and Ala; and the residue in the P3' position is an amino acid residue selected from the group consisting of His, Ser, Lys, and Ala, wherein:

said depsipeptide is cleanable into an N-terminal fragment and a C-terminal fragment by NS3 serine protease of hepatitis C virus (HCV) in said ester bond between residue P1 and residue P1' with a $k_{cat}/K_m$ greater than 20 $M^{-1}$ $S^{-1}$;

the N-terminal residue is optionally modified with an α-amino protecting group;

the C-terminal residue is optionally modified at a side chain or at the carboxyl group;

an amino acid residue in said C-terminal fragment portion of said depsipertide is optionally radiolabeled; and optionally, either (1) an amino acid residue in said N-terminal fragment portion of said depsipeptide is modified with a fluorescent 5-[(2'-aminoethyl)amino] naphthalene-sulfonic acid donor group (EDANS) and an amino acid residue in said C-terminal fragment portion of said depsipeptide is modified with a 4-[[4'-dimethylaminophenyl]azo]benzoic acid acceptor group (DABCYL) or (2) an amino acid residue in said N-terminal fragment portion of said depsipeptide is modified with DABCYL and an amino acid residue in said C-terminal portion of said depsipeptide is modified with EDANS.

2. The depsipeptide according to claim 1, wherein said depsipeptide is cleavable by the NS3 protease of HCV virus with a $k_{cat/km}$ greater than 2780 $M^{-1}$ $S^{-1}$.

3. The depsipeptide according to claim 2, wherein said depsipeptide has a sequence selected from the group consisting of SEQ ID NOs:42–46.

4. A method for reproducing in vitro the proteolytic activity of the hepatitis C virus (HCV) NS3 protein, comprising contacting an isolated and purified polypeptide having the protease activity of HCV NS3 protein with the depsipeptide of claim 1.

5. The method according to claim 4, wherein said depsipeptide is cleavable by the NS3 protease of HCV virus with a $k_{cat}/K_m$ greater than 2780 $M^{-1}S^{-1}$.

6. The method according to claim 4, wherein said depsipeptide has a sequence selected from the group consisting of SEQ ID Nos:42–46.

7. The method according to claim 4, wherein said depsipeptide is used in a high-throughput assay at a concentration below 2 nM.

8. The method according to claim 4, further comprising continuous monitoring of the proteolytic activity of the polypeptide having the activity of NS3 protease of HCV with a desipeptide having an internal fluorogenic quenching by Resonance Energy Transfer between a fluorescent donor, 5-[(2'-aminoethyl)amino]naphthalene-sulfonic acid (EDANS), adjacent to one end of the depsipeptide, and an acceptor group, 4-[[4'-(dimethylaminophenyl]azo]benzonic acid (DABCYL) adjacent to the other end of the depsipeptide.

* * * * *